United States Patent
Tromanhauser et al.

(10) Patent No.: US 7,060,068 B2
(45) Date of Patent: *Jun. 13, 2006

(54) VERTEBRAE FASTENER PLACEMENT GUIDE

(75) Inventors: Scott G. Tromanhauser, Salem, MA (US); Bret M. Berry, Cordova, TN (US); Eric C. Lange, Germantown, TN (US); Eddie F. Ray, III, Collierville, TN (US)

(73) Assignee: SDGI Holdings, Inc., Wilmington, DE (US)

( * ) Notice: Subject to any disclaimer, the term of this patent is extended or adjusted under 35 U.S.C. 154(b) by 71 days.

This patent is subject to a terminal disclaimer.

(21) Appl. No.: 10/748,120

(22) Filed: Dec. 30, 2003

(65) Prior Publication Data

US 2004/0230202 A1    Nov. 18, 2004

Related U.S. Application Data

(63) Continuation of application No. 09/695,004, filed on Oct. 24, 2000, now Pat. No. 6,669,698.

(51) Int. Cl.
  *A61B 17/56* (2006.01)
(52) U.S. Cl. ......................... 606/61; 606/96
(58) Field of Classification Search ............. 606/61, 606/96, 104
  See application file for complete search history.

(56) References Cited

U.S. PATENT DOCUMENTS

| | | |
|---|---|---|
| 4,159,716 A | 7/1979 | Borchers |
| 4,257,411 A | 3/1981 | Cho |
| 4,667,664 A | 5/1987 | Taylor et al. |
| 4,708,139 A | 11/1987 | Dunbar, IV |
| 4,714,076 A | 12/1987 | Comte et al. |
| 4,722,331 A | 2/1988 | Fox |
| 4,901,711 A | 2/1990 | Goble et al. |
| 4,957,495 A | 9/1990 | Kluger |
| 4,997,434 A | 3/1991 | Seedhom et al. |
| 5,013,317 A | 5/1991 | Cole et al. |
| 5,112,337 A | 5/1992 | Paulos et al. |
| 5,154,720 A | 10/1992 | Trott et al. |
| 5,163,940 A | 11/1992 | Bourque |
| 5,178,621 A | 1/1993 | Cook et al. |
| 5,312,412 A | 5/1994 | Whipple |
| 5,458,602 A | 10/1995 | Goble et al. |
| 5,527,312 A | 6/1996 | Ray |
| 5,558,674 A | 9/1996 | Heggeness et al. |
| 5,584,839 A | 12/1996 | Gieringer |

(Continued)

FOREIGN PATENT DOCUMENTS

DE    297 03 947 U1    7/1997

(Continued)

OTHER PUBLICATIONS

*Posterior Techniques*; Stabilization Techniques, Thoracolumbar Spine; publication unknown.

(Continued)

*Primary Examiner*—Roy D. Gibson
(74) *Attorney, Agent, or Firm*—Krieg DeVault, LLP

(57) ABSTRACT

A screw placement guide includes a first member having a first guide adapted to contact a first vertebral bone portion and a second member having a second guide adapted to contact a second vertebral bone portion. A clamping mechanism provided on one of the members clamps the first guide and the second guide to the vertebral bone portions. The first guide and the second guide are aligned in order to indicate how a fastener will be aligned when fastened between adjacent vertebrae. A driver engages clamping mechanism to clamp the two members together.

27 Claims, 24 Drawing Sheets

U.S. PATENT DOCUMENTS

| | | | |
|---|---|---|---|
| 5,613,971 | A | 3/1997 | Lower et al. |
| 5,658,293 | A | 8/1997 | Vanlaningham |
| 5,725,532 | A | 3/1998 | Shoemaker |
| 5,741,266 | A | 4/1998 | Moran et al. |
| 5,895,390 | A | 4/1999 | Moran et al. |
| 5,941,706 | A | 8/1999 | Ura |
| 6,019,767 | A | 2/2000 | Howell |
| 6,056,749 | A | 5/2000 | Kuslich |
| 6,066,142 | A | 5/2000 | Serbousek et al. |
| RE36,758 | E | 6/2000 | Fitz |
| 6,120,511 | A | 9/2000 | Chan |
| 6,187,011 | B1 | 2/2001 | Torrie |
| 6,210,415 | B1 | 4/2001 | Bester |
| 6,254,604 | B1 | 7/2001 | Howell |
| 6,287,309 | B1 | 9/2001 | Baccelli et al. |
| 6,287,313 | B1 | 9/2001 | Sasso |
| 6,342,056 | B1 | 1/2002 | Mac-Thiong et al. |
| 6,669,698 | B1 | 12/2003 | Tromanhauser et al. |

FOREIGN PATENT DOCUMENTS

| | | |
|---|---|---|
| DE | 198 11 354 A1 | 9/1999 |
| WO | WO 93/22975 | 11/1993 |
| WO | WO 00/62684 | 10/2000 |

OTHER PUBLICATIONS

*Selective Decompression and Translaminar Articular Facet Screw Fixation for Lumbar Canal Stenosis and Disc Protrusion*; Benini, Magerl; British Journal of Neurosurgery (1993) 7, 413-418.

*Stability of the Lumbar Spine and Method of Instrumentation*; Vanden Berghe, Mehdian, Lee, Weatherley; Acta Orthopaedica Belgica, vol. 59-2, (1993).

*Biomechanical Evaluation of Translaminar Facet Joint Fixation*; Deguchi, Chang, Sato, Matsuyama, Zdeblick; Spine, vol. 23, No. 12 (1998) pp. 1307-1313.

*Lumbosacral Fushion Using Internal Fixation with a Spinous Process for the Graft*; Graham; Clinical Orthopaedics and Related Research, No. 140, May 1979, pp. 72-77.

*Translaminar Screw Fixation in the Lumbar Spine: Technique, Indications, Results*; Grob, Humke; Eur Spine J (1998) 7: 178-186.

*Translaminar Facet Joint Screw Fixation for Lumbar and Lumbosacral Fusion, A Clinical and Biomechanical Study*; Heggeness, Esses; From the Center for Spinal Disorders, Division of Orthopaedics, Baylor College of Medicine, Houston, Texas, and Dewar Spine Unit, Department of Surgery, University of Toronto, Toronto, Ontario, Canada, pp. S266-S269, Nov. 1, 1990.

*Translaminar Screw Fixation of the Lumbar and Lumbosacral Spine*; Humke, Grob, Dvorak, Messikommer; Spine, vol. 23; pp. 1180-1184, Nov. 10, 1998.

*Enhancement of Lumbar Spine Fushion by Use of Translaminar Facet Joint Screws*; Jacobs, Montesano, Jackson; Spine, vol. 14, No. 1, pp. 12-15, (1989).

*Arthrodesis with Facet Screws*; Jeanneret; Lumbosacral and Spinopelvic Fixation, Edited by Joseph Y. Margulies, et al., (1996).

*Translaminar Facet Screw Placement: and Anatomic Study*; Lu, Ebraheim, Yeasting; The American Journal of Orthopedics, pp. 550-555; Aug. 1998.

*Lumbar Degenerative Spondylolisthesis: Review of 106 Operated Cases with Degenerative Anterior Vertebral Translation as the Predominant Aspect of the Spondylosis*: Plotz, Benini; Neurosurgery Quarterly, vol. 8, No. 4, pp. 271-287 (1998).

*The role of Supplemental Translaminar Screws in Anterior Lumbar Interbody Fixation: A Biomechanical Study*; Rathonyi, Oxland, Gerich, Grassmann, Nolte; Eur Spine J (1998) 7: 400-407.

*Translaminar Facet Screw Fixation in Lumbar Spine Fusion*; Reich, Kuflik, Neuwirth; Spine, vol. 18, pp. 444-449; No. 4 (1993).

*Posterior Lumbar Interbody Fusion with Facet-Screw Fixation*; Stonecipher, Wright; Spine, vol. 14, No. 4, pp. 468-471 (1989).

*Surgical Treatment of Internal Disc Disruption: An Outcome Study of Four Fusion Techniques*; Vamvanij, Fredrickson, Thorpe, Stadnick, Yuan; Journal of Spinal Disorders, vol. 11, No. 5, pp. 375-382, (1998).

*Interbody Implant and Translaminar Screw Fixation Contrasted Helical Axes of Motion*; Oxland, Rathonyi, Frei Nolte; (No date information given).

*Transfacet Screws with Lumbar Interbody Reconstruction: BIomechanical Study of Motion Segment Stiffness*; Volkman, Hutton; Journal of Spinal Disorders, vol. 9, No. 5, pp. 425-432 (1996).

VERTEBRAE FASTENER PLACEMENT GUIDE

REFERENCE TO RELATED APPLICATIONS

This application is a continuation U.S. patent application Ser. No. 09/695,004, filed Oct. 24, 2000, now U.S. Pat. No. 6,669,698, issued Dec. 30, 2003, which is hereby incorporated by reference in its entirety.

BACKGROUND OF THE INVENTION

The present invention generally relates to fastener guides, and more specifically, but not exclusively, concerns an apparatus and method for fixing a portion of a spine with a fastener.

In the realm of orthopedic surgery, it is well known to use screws to fix the position of bones. In this way, the healing of a broken bone can be promoted and malformation or other injuries can be corrected. For example, in the field of spinal surgery, there are a number of reasons for fixing a portion of the spine with screws, including (a) to correct abnormal curvature of the spine, including a scoliotic curvature, (b) to maintain appropriate spacing and provide support to broken or otherwise injured vertebrae, and (c) to perform other therapies on the spinal column.

Traditional surgical treatment of lumbar spinal stenosis and disc protrusion consists of a wide decompression and discectomy. Osteophite is an attempt by the body to stabilize motion segments by stiffening components of the body. Spinal fusion tries to achieve the same effect. Selective decompression along with translaminar screw fixation is used to fix adjacent vertebrae and fuse them together.

In the translaminar procedure, the screw is passed through the facets and laminae of adjacent vertebrae in order to fix the adjacent vertebrae together. During the procedure, there always exists a danger of injuring the spinal column by not aiming the drill and screw correctly. The procedure is further complicated by the tight operating space. Only a limited number of hands can have access to the tight operating space. Complications, such as spinal damage, can also ensue if a screw with an improper length is used to fix the adjacent vertebrae together. Therefore, there has been a long felt need for a device to provide precise hands free guidance of screws through the spine and that allows a surgeon to see the exact trajectory and required length of a screw prior to fastening the vertebrae together.

SUMMARY OF THE INVENTION

One form of the present invention is a unique fastener placement guide. Another form concerns a unique method for fixing two vertebrae together.

A further form of the present invention is directed to a unique apparatus for guiding a fastener that fastens a first vertebral bone portion with a second vertebral bone portion. The apparatus includes a first member having a first guide adapted to contact the first vertebral bone portion. A second member has a second guide that is aligned with the first guide and adapted to contact the second vertebral bone portion. A clamping mechanism is provided between the first and second members to clamp the first guide and the second guide to the respective bone portions. The first and second guides indicate fastener alignment.

Another form of the present invention is directed to a unique method for fastening two vertebrae together. A fastener placement apparatus has a first member with a first guide, a second member with a second guide aligned with the first guide, and a clamping mechanism to clamp the members together. The first and second guides are aligned along two vertebral bone portions. The two bone portions are clamped together with the first and second members. The two bone portions are fastened together with a fastener that is in alignment with the first and second guides.

DESCRIPTION OF THE PREFERRED EMBODIMENTS

Figure 1:
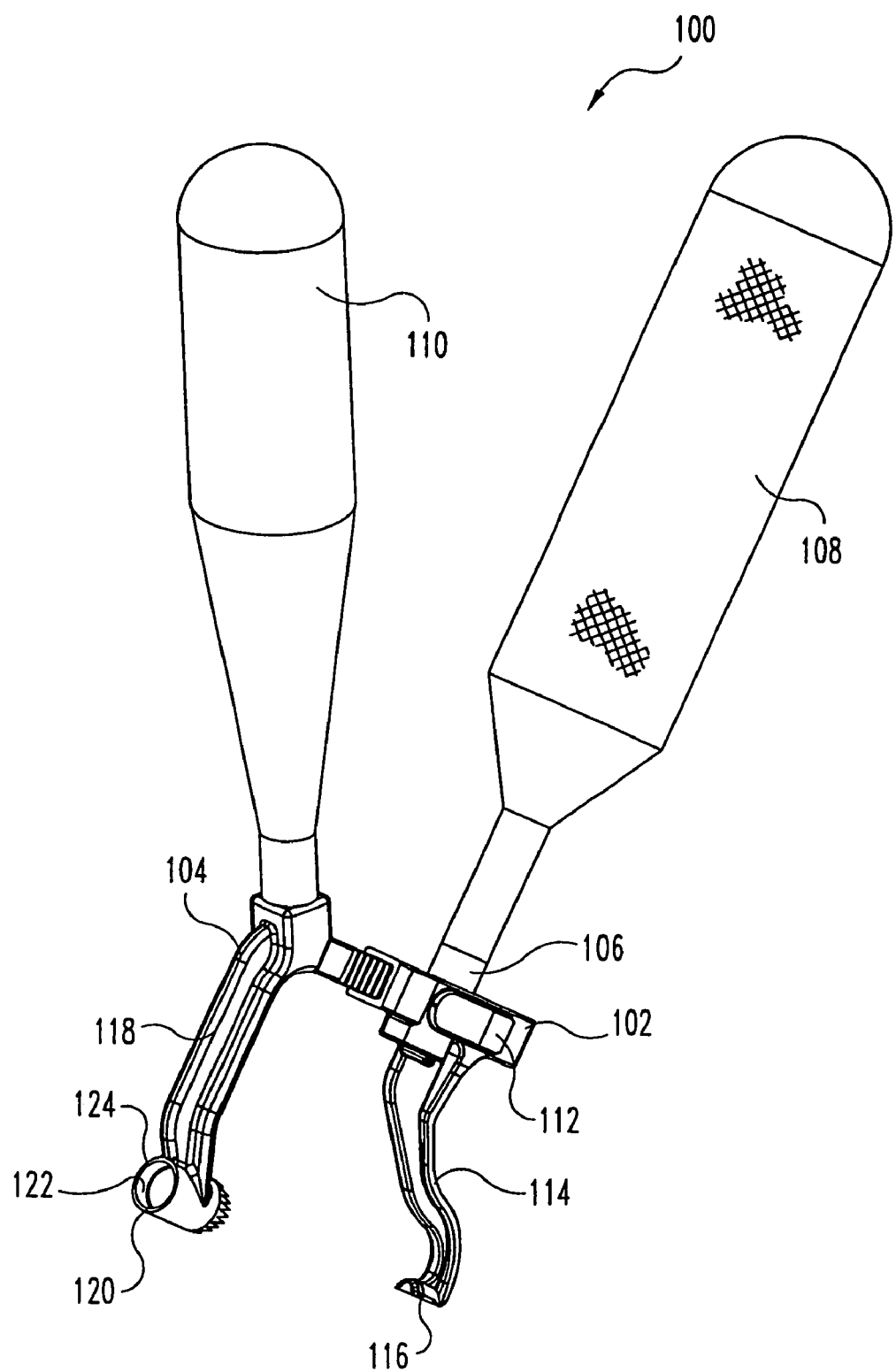
FIG. 1 is a perspective view of a screw placement guide according to one embodiment of the present invention.

For the purposes of promoting an understanding of the principles of the invention, reference will now be made to the embodiments illustrated in the drawings and specific language will be used to describe the same. It will nevertheless be understood that no limitation of the scope of the invention is thereby intended. Any alterations and further modifications in the described embodiments, and any further applications of the principles of the invention as described herein are contemplated as would normally occur to one skilled in the art to which the invention relates. One embodiment of the invention is shown in great detail, although it will be apparent to those skilled in the art that some of the features which are not relevant to the invention may not be shown for the sake of clarity.

Figure 2:
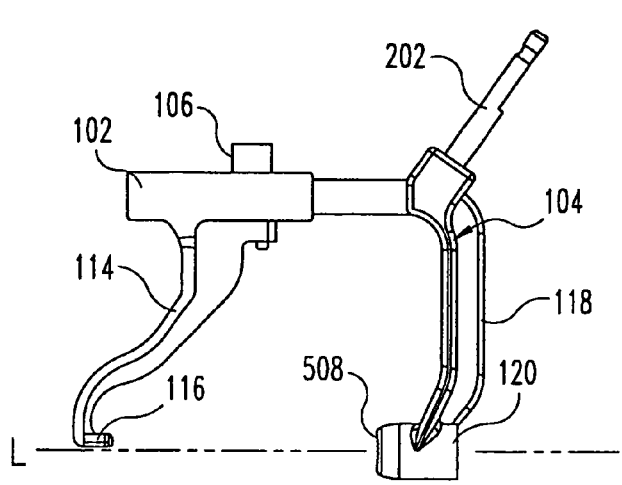
FIG. 2 is a side view of the screw placement guide of FIG. 1 without a handle and a driver.

FIG. 1 shows a perspective view of a screw placement guide 100 according to one embodiment of the present invention. The placement guide 100 includes a first (driving) member 102, and a second (clamping) member 104. A clamping mechanism 106 moveably couples the first member 102 with the second member 104. A driver 108 is removably coupled to clamping mechanism 106, and a handle 110 is removably coupled to a handle coupling member 202 that extends from the second member 104 (FIG. 2). Driver 108 and handle 110 can be removed from guide 100 in order to reduce obstructions during surgery. It should be appreciated, however, that driver 108 and handle 110 can also be permanently attached to guide 100. A locking mechanism 112 is provided on the first member 102. Driver 108 is used to drive the clamping mechanism 106 in order to clamp the members 102 and 104 together. Locking mechanism 112 is used to lock the relative positions between the members 102 and 104.

First member 102 has a first support arm 114 that supports an arcuate guide member 116. The arcuate cylindrical shape of guide 116 helps to minimize the size of the incision required in order to locate guide 116. Second member 104 includes a support arm 118 and a cylindrical guide member 120. Cylindrical guide member 120 is adapted to receive a guide tube. Guide 120 has a bore 122 defined therein. Bore 122 has a conical entry surface 124 that is adapted to receive a guide tube.

Figure 3:
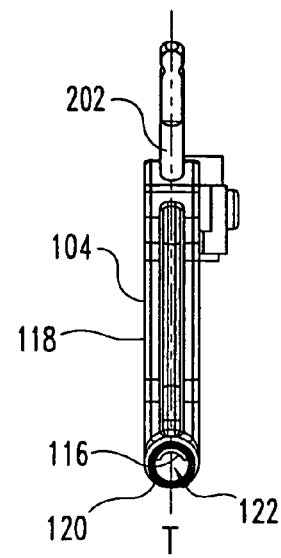
FIG. 3 is an end view of the screw placement guide of FIG. 2.

As illustrated in FIG. 2, guides 116 and 120 are aligned along longitudinal axis L. As shown in FIG. 3, the guides 116 and 120 are also aligned along transverse axis T. During surgery, this alignment of guides 116 and 120 along both the longitudinal L and transverse T axes is used to indicate the alignment of a screw that is to be fastened through screw placement guide 100.

Figure 4:
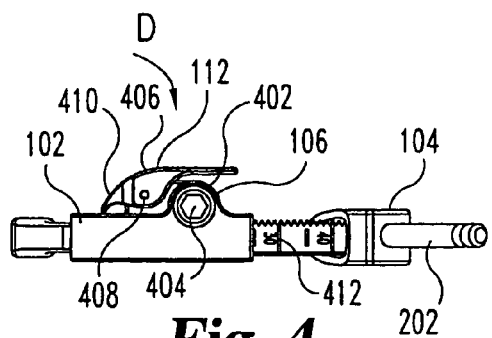
FIG. 4 is a top view of the screw placement guide of FIG. 2.

Clamping mechanism 106, as shown in FIG. 4, includes a pinion 402 that is received within first member 102. Pinion 402 has a driver engagement recess 404, which is adapted to be engaged and rotated by driver 108. Locking mechanism 112 includes a locking lever 406 pivotally mounted to first member 102 by pin 408. Lever 406 further has a rack-engaging portion 410, which is adapted to lock against second member 104. Lever 406 is spring biased to lock first and second members 102, 104 into position. When lever 406 is pivoted in direction D, second member 104 is unlocked so that second member 104 can be moved by clamping mechanism 106. Locking lever 406 can also include a spring for biasing lever 406 to the locked position. Second member 104 further has fastener length markings 412 that indicate the length of the required fastener.

Figure 5:
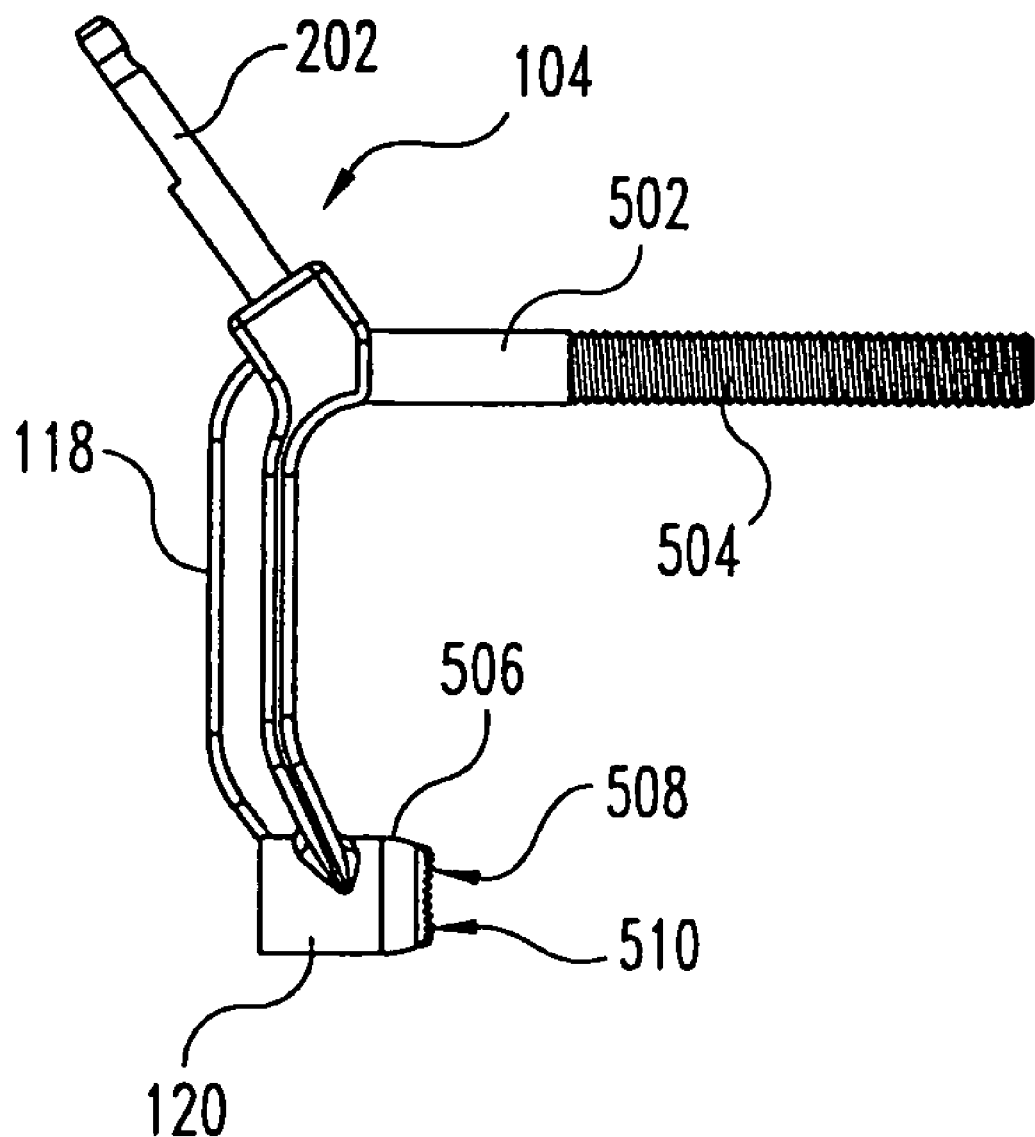
FIG. 5 is a side view of one member shown in FIG. 1.

Second member 104, as shown in FIG. 5, has a clamping arm 502 that is coupled to clamping mechanism 106 on the first member 102. Arm 502 has a gear tooth rack portion 504 that engages pinion gear 402 in clamping mechanism 106. Rack portion 504 along with pinion gear 402 form a rack and pinion mechanism that is used to generate a clamping motion to clamp an object or objects between the first member 102 and second member 104. As shown, guide 120 further includes a conical outer surface 506 and a bone engaging surface 508 at an end. Bone engaging surface 508 has serrations 510, which minimize slippage of the bone engaging surface 508 against bone. The conical shape of outer surface 506 allows guide 120 to have a sharp bone engaging surface 508 in order to dig into bone.

Figure 6:
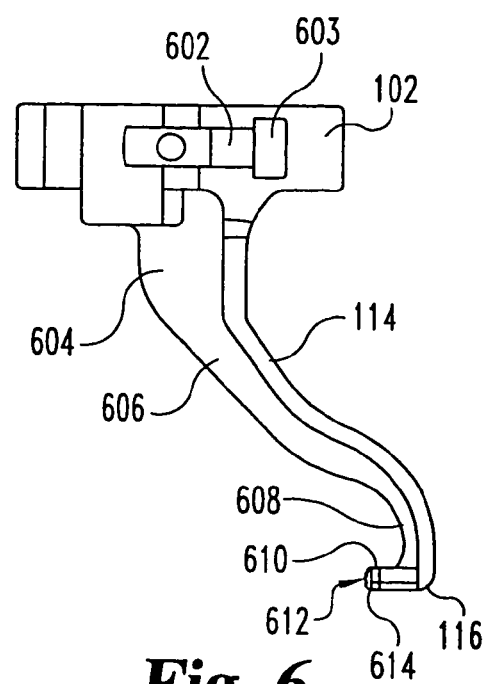
FIG. 6 is a side view of another member shown in FIG. 1.

As shown in FIG. 6, first member 102 includes a lever mounting portion 602 at which locking lever 406 is pinned to first member 102. Further, first member 102 has a lever receiving opening 603 through which rack engaging portion 410 of lever 406 is received and engages rack portion 504 of second member 104. Support arm 114 is shaped so that the size of an incision in a patient can be minimized. As shown, support arm 114 has a substantially straight portion 604, an angled portion 606, and a guide connecting portion 608. Guide 116 has a semi-cylindrical shape in order to allow guide 116 to engage a vertebra in a narrow area such as between facet and transverse process. Guide 116 includes a semi-conical portion 610, and a vertebra engaging end 612 with serrations 614. Conical portion 610 and serrations 614 help to minimize slippage of guide 116 against bone.

Figure 7:
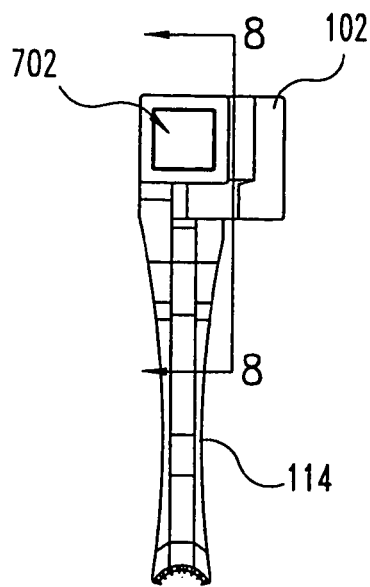
FIG. 7 is an end view of the first member shown in FIG. 6.
Figure 8:
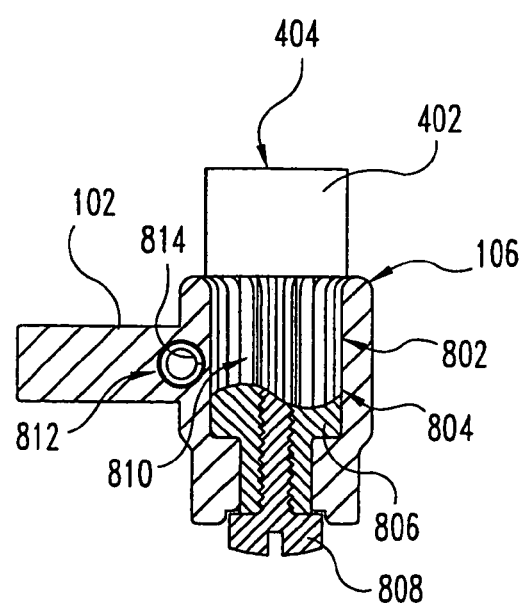
FIG. 8 is a partial cross-sectional view of a portion of the first member shown in FIG. 6 and taken at line 8—8 in FIG. 7 and viewed in the direction of the arrows.

First member 102 in FIG. 7 further includes a clamping arm receiving aperture 702 in which clamping arm 502 of the second member 104 is received. An enlarged cross-sectional view taken at line 8—8 in FIG. 7 showing a portion of clamping mechanism 106 is shown in FIG. 8. First member 102 has a pinion receiving hole 802 defined therein. Hole 802 is adapted to receive pinion 402. In one form, hole 802 includes a wide cylindrical portion 804 and a narrow cylindrical portion 806. A ratchet connector (screw) 808 is coupled to cylindrical portion 804 in order to secure the pinion 402 in hole 802. Pinion 402 has teeth 810 that engage the teeth of rack portion 504 of second member 104. First member 102 further has a spring cavity 812 that receives bias coil spring 814. Bias spring 814 biases lever 406 into the locked position.

Figure 9:
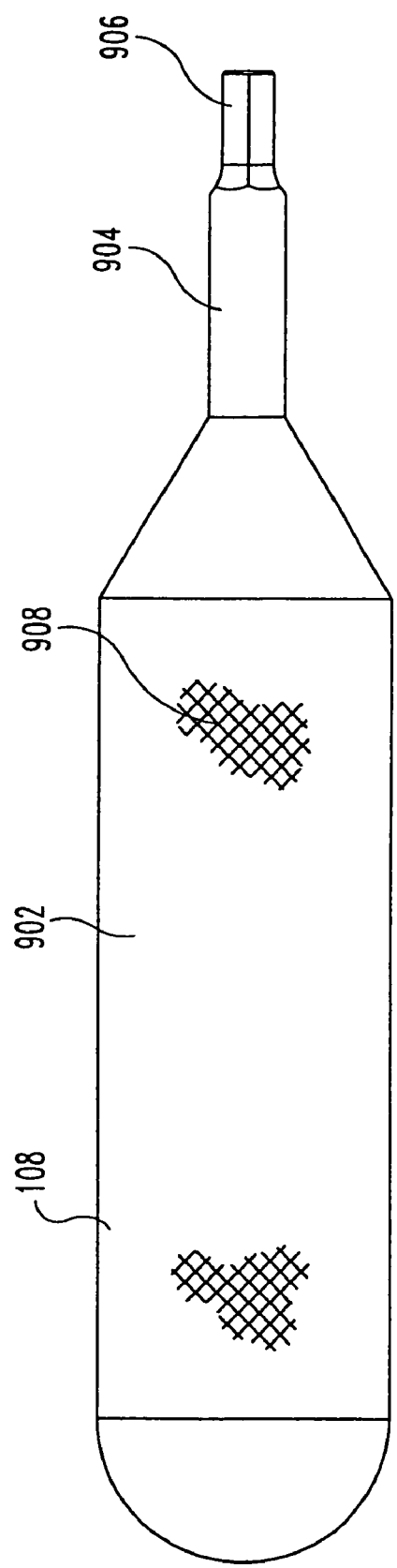
FIG. 9 is a side view of the driver shown in FIG. 1.

Driver 108 according to one embodiment of the present invention is shown in FIG. 9. Driver 108 includes a handle portion 902, a connector 904 coupled to handle portion 902, and a pinion engaging portion 906 coupled to connector 904. Pinion engaging portion 906 is coupled to driver engagement recess 404 of pinion 402. In one particular form, pinion-engaging portion 906 has a hexagonal cross-sectional shape. It should be appreciated that pinion-engaging portion 906 can have other generally known cross-sectional shapes. In order to improve the grip for a surgeon, handle portion 902 has knurling 908. It should be understood that the present invention can include other types of drivers that are generally known by those skilled in the art. For example, instead of a manual driver, an automatic driver can be used.

Figure 10:
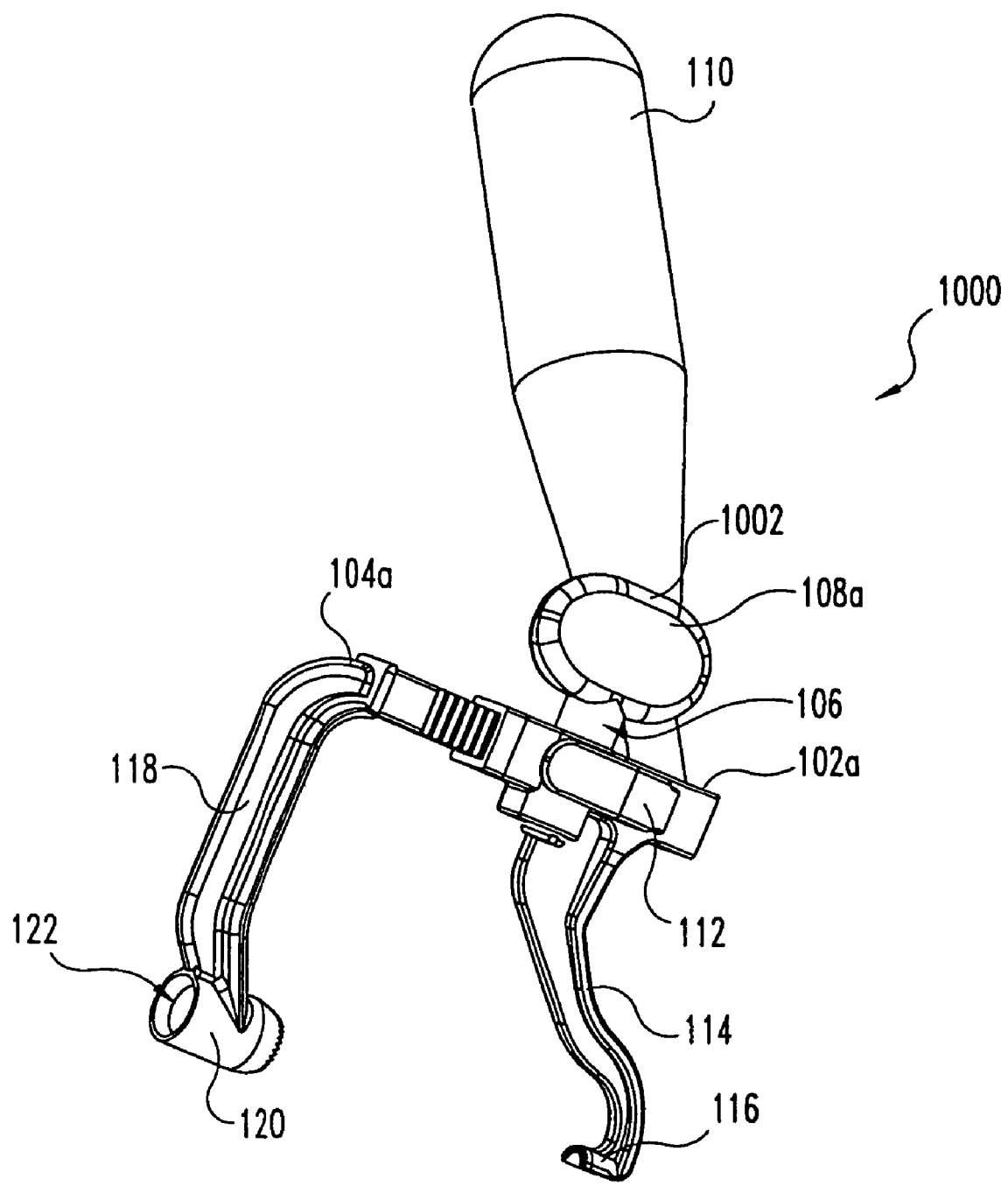
FIG. 10 is a perspective view of a screw placement guide according to another embodiment of the present invention.
Figure 11:
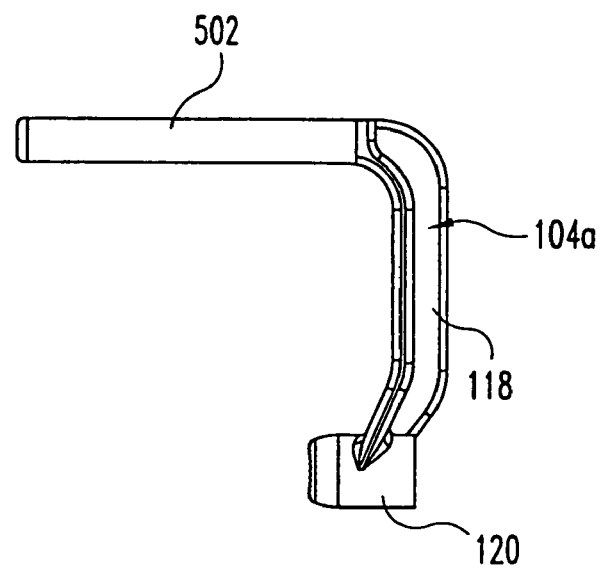
FIG. 11 is a side view of one member shown in FIG. 10.
Figure 12:
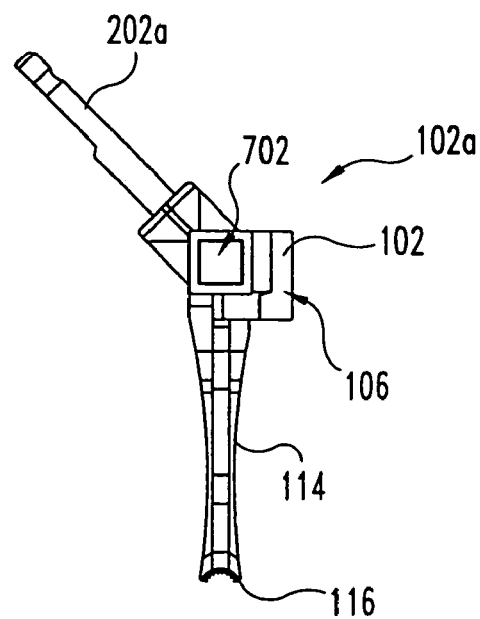
FIG. 12 is an end view of another member shown in FIG. 10.
Figure 14:
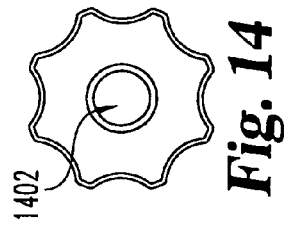
FIG. 14 is an end view of the guide tube shown in FIG. 13.

A screw placement guide 1000 according to another embodiment of the present invention is shown in FIG. 10. In the embodiment illustrated in FIG. 10, handle 110 is coupled to first member 102a instead of second member 104a. Driver 108a has an elliptical shaped handle portion 1002. As shown in FIG. 11, second member 104a does not include handle coupling member 202. Instead, as shown in FIG. 12, first member 102a has a handle-coupling member 202a. In order to improve the ergonomics, handle-coupling member 202a is coupled to first member 102a at an angle with respect to support arm 114. As shown in FIGS. 10 and 12, handle-coupling member 202 along with handle 110 are oriented at an angle so as to not interfere with rotation of driver 108a and to relieve stress in a wrist of a surgeon.

Figure 13:
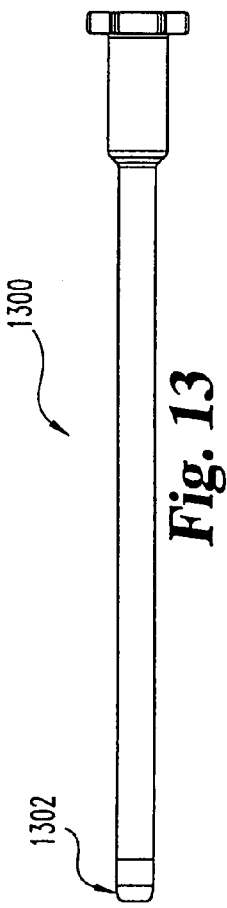
FIG. 13 is a side view of a guide tube.
Figure 15:
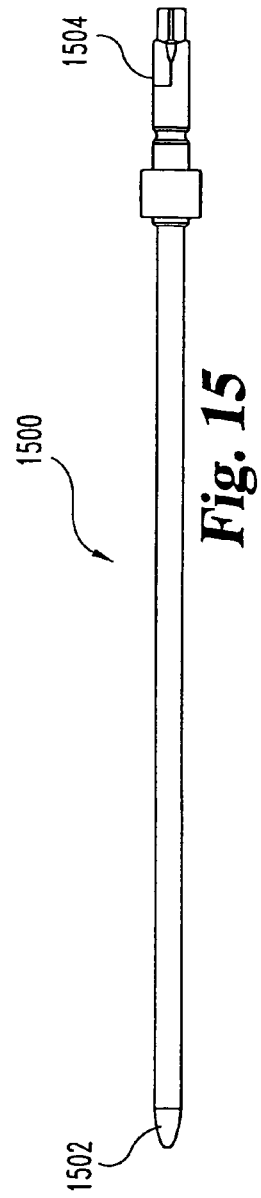
FIG. 15 is a side view of a trocar.
Figure 16:
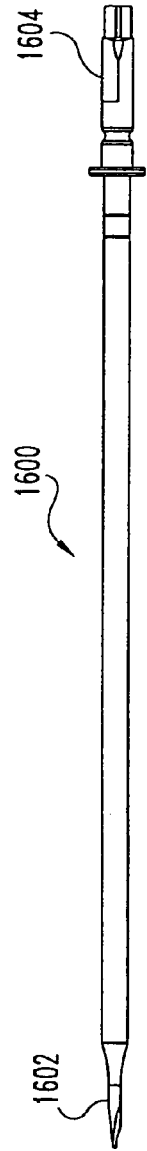
FIG. 16 is a side view of an awl.

A guide tube 1300, as shown in FIG. 13, has a coupling end 1302 adapted to couple into guide 120 of the second member 104 or 104a. Guide tube 1300 has a hole 1402 of which is adapted to receive instruments. One such type of instrument is a trocar 1500, which is shown in FIG. 15. Trocar 1500 has a pointed end 1502 which aids during insertion. Trocar 1500 further includes a coupling end 1504 adapted to couple to a handle and/or other types of generally known mechanisms.

Figure 17:
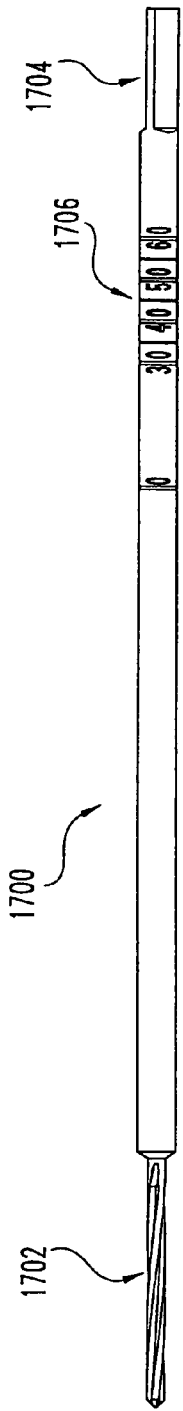
FIG. 17 is a side view of a drill bit.
Figure 18:
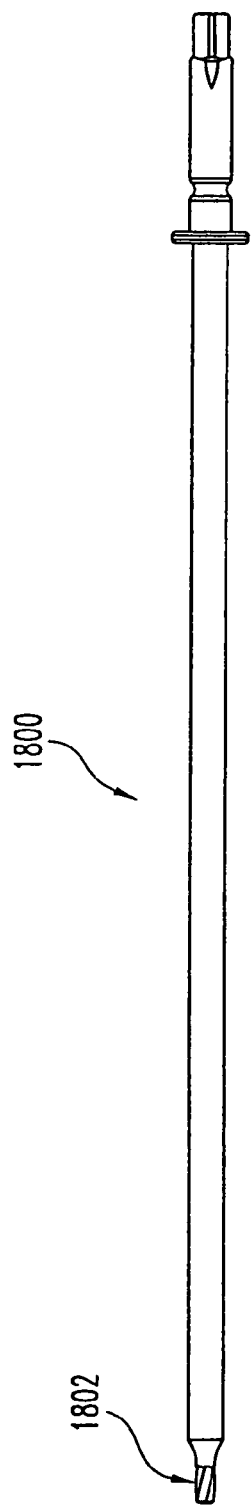
FIG. 18 is a side view of a screwdriver.
Figure 20:
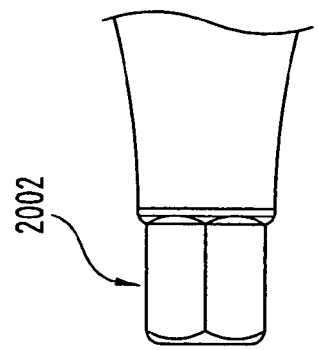
FIG. 20 is an enlarged side view of an end of a screwdriver according to another embodiment.
Figure 19:
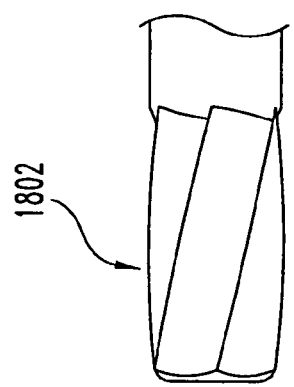
FIG. 19 is an enlarged side view of one end of the screwdriver shown in FIG. 18.

Other types of instruments that can also be inserted into guide tube 1300 are shown in FIGS. 16–20. Awl 1600 includes a pointed end 1602 and a coupling end 1604 that is adapted to couple to a handle and/or other types of generally known mechanisms. As illustrated in FIG. 17, drill bit 1700 includes a cutting portion 1702, a drill engaging portion 1704, and depth markings 1706. A screwdriver 1800 according to one embodiment is shown in FIG. 18. Screwdriver, 1800 has a screw-engaging portion 1802 that is adapted to couple to a screw. An enlarged view of screw coupling portion 1802 is shown in FIG. 19. As shown, screw-coupling portion 1802 in one embodiment has a "self-retaining configuration" that prevents slippage of the screwdriver from a screw. A coupling portion 2002 according to another embodiment has a hexagonal cross-sectional shape with straight walls that couple to a screw.

A method for fixing adjacent vertebrae according to one embodiment of the present invention will now be described with reference to FIGS. 21–29. Although the method is described in reference to fixing separate vertebrae together, it should be appreciated that screw placement guide 100 can be used to fasten together a single fractured vertebra. It should also be understood that other types of generally known fasteners, besides screws, can be used in conjunction with placement guides 100 and 1000 in order to fasten vertebral bone portions together.

Figure 21:
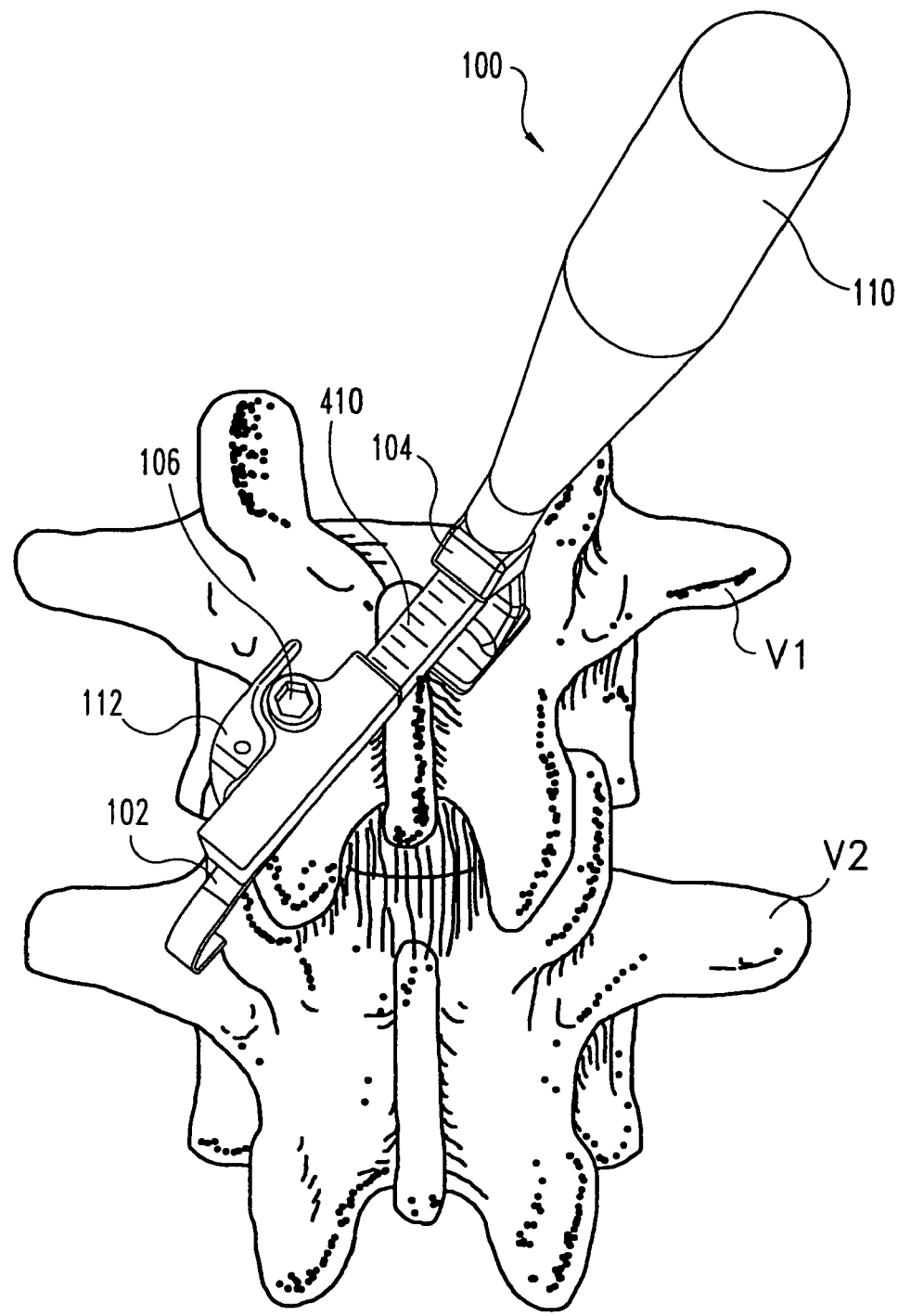
FIG. 21 is a top view of the screw placement guide of FIG. 1 clamped to adjacent vertebrae.
Figure 22:
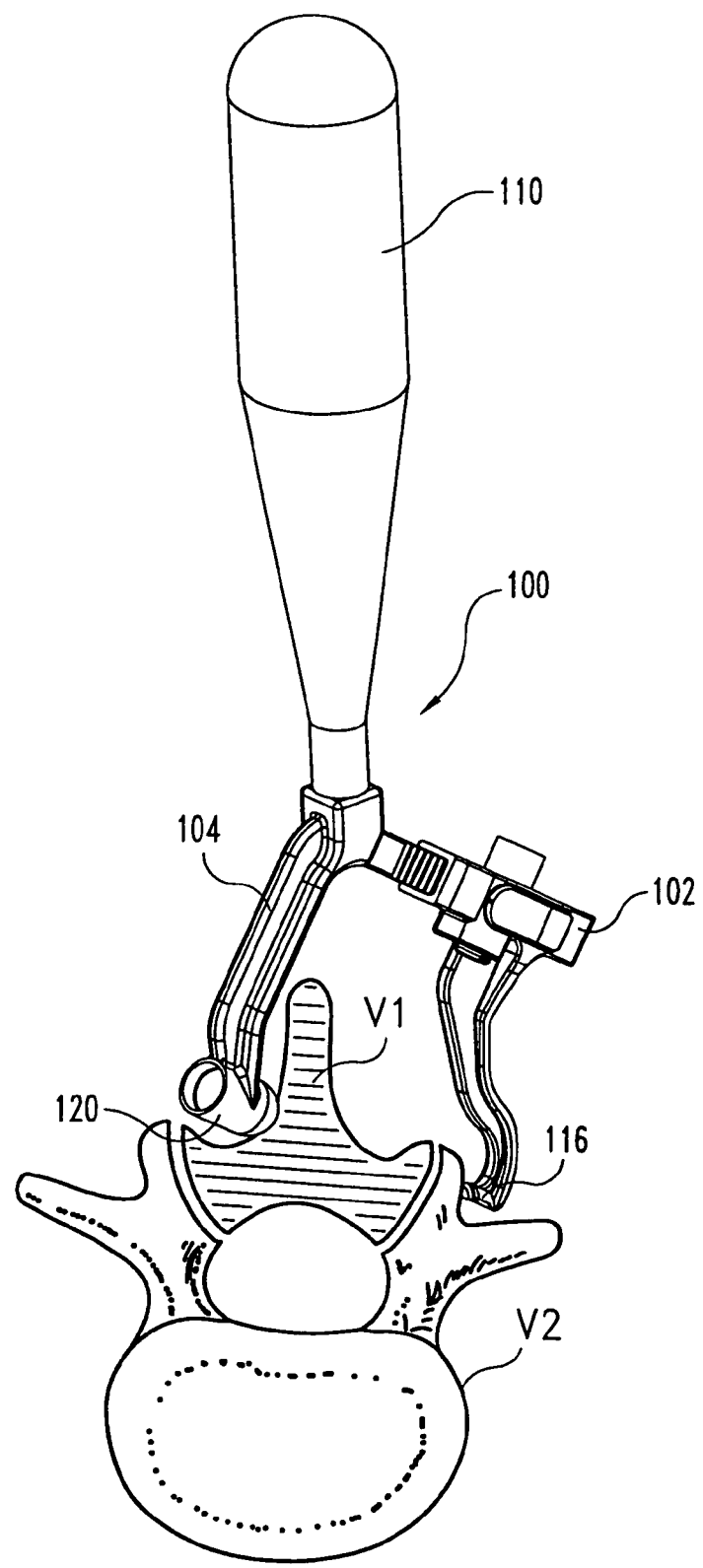
FIG. 22 is a partial cross-sectional view of a vertebra showing the screw placement guide of FIG. 1 clamped to adjacent vertebrae.
Figure 23:
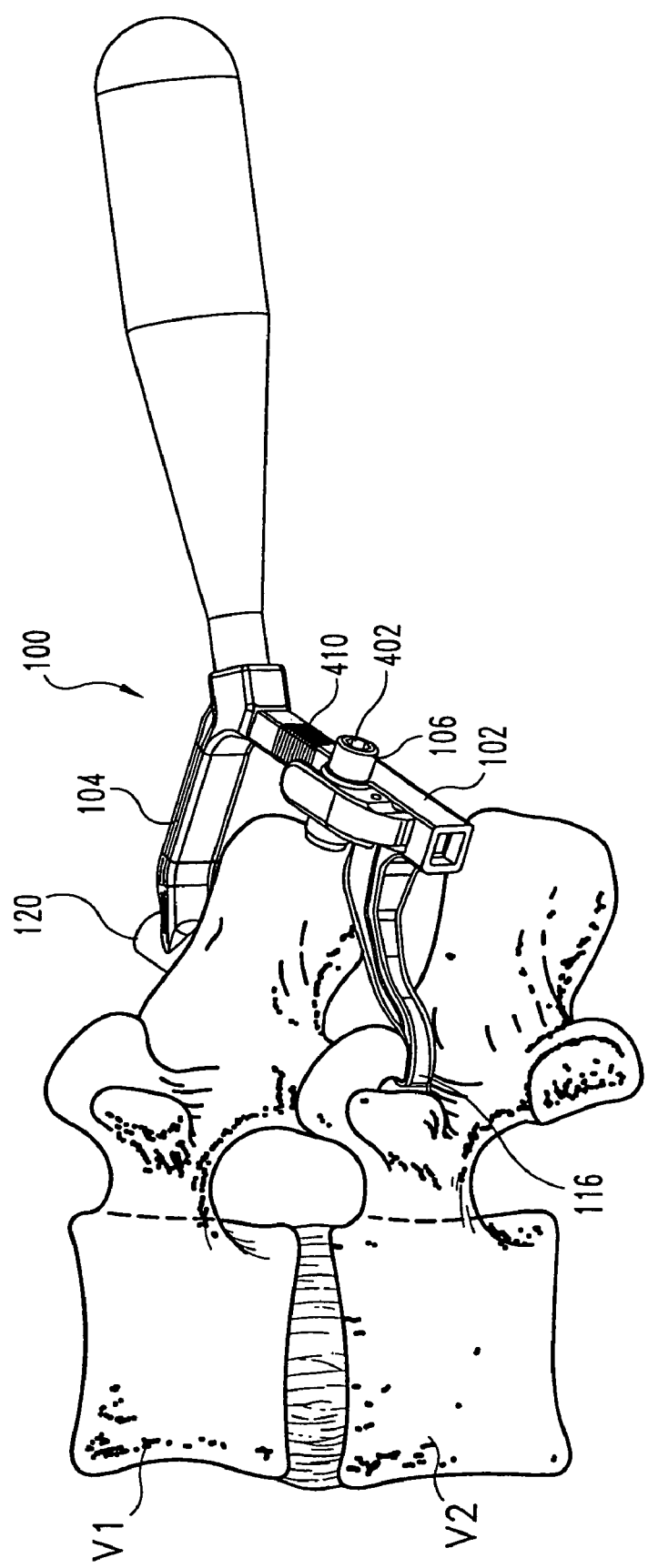
FIG. 23 is a side view of the screw placement guide of FIG. 1 clamped to adjacent vertebrae.
Figure 24:
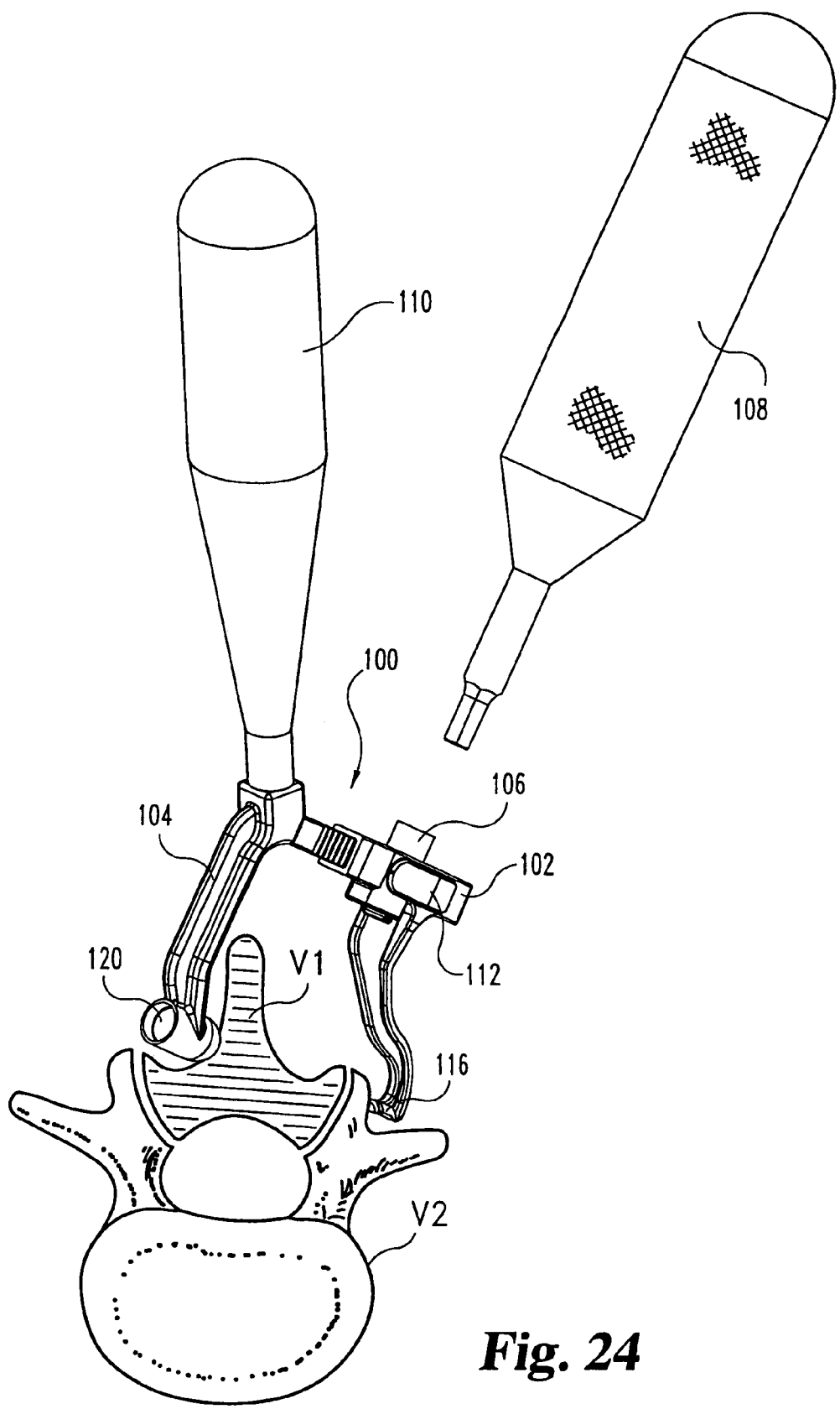
FIG. 24 is a partial cross-sectional view through a vertebra showing the screw placement guide of FIG. 1 along with a driver.

As shown in FIGS. 21–23, screw placement guide 100 is aligned along adjacent vertebrae V1 and V2. Arcuate guide 116 allows guide 100 to couple to irregular shaped portions of vertebra V2, such as between facet and transverse process. Further, the arcuate shape of guide 116 reduces the amount of tissue that needs to be cut and moved. Arcuate guide 116 is positioned on vertebra V2 at a desired fastener exit point. Guide 120 is then positioned at a desired fastener entry point on vertebra V1. Driver 108 in FIG. 24 is coupled to the socket of pinion 402 of clamping mechanism 106 in order to clamp the guides 116 and 120 to the vertebrae V1 and V2. Once screw placement guide 100 is properly positioned, driver 108 is rotated and drives clamping mechanism 106 in order to clamp guides 116 and 120 of screw placement guide 100 to the vertebrae V2 and V1, respectively. Locking mechanism 112 locks members 102 and 104 into position relative to each other. Guides 116 and 120 of screw placement guide 100 allow the surgeon to visualize the alignment of the screw before clamping tightly and then fastening the two vertebrae V1 and V2 together. A surgeon can unclamp and reposition screw placement guide 100 before installing screws, in order to avoid the damaging the spine. Since the screw placement guide 100 can be clamped and unclamped at different lengths, the screw placement guide 100 can be adjusted to accommodate various types of anatomy. For example, the screw placement guide 100 can be adjusted to accommodate varying spinous process heights.

Since screw placement guide 100 is clamped to the vertebrae V1 and V2, screw placement guide 100 provides hands free guidance. In addition, the clamping ensures that the vertebrae V1 and V2 are tightly compressed against one another in order to improve fastening. After screw placement guide 100 is clamped to vertebrae V1 and V2, driver 108 can be removed so as to reduce the number of obstructions in the operating area. The surgeon selects the proper screw length for joining the adjacent facets of vertebrae V1 and V2 by reading length indicator 410.

Figure 25:
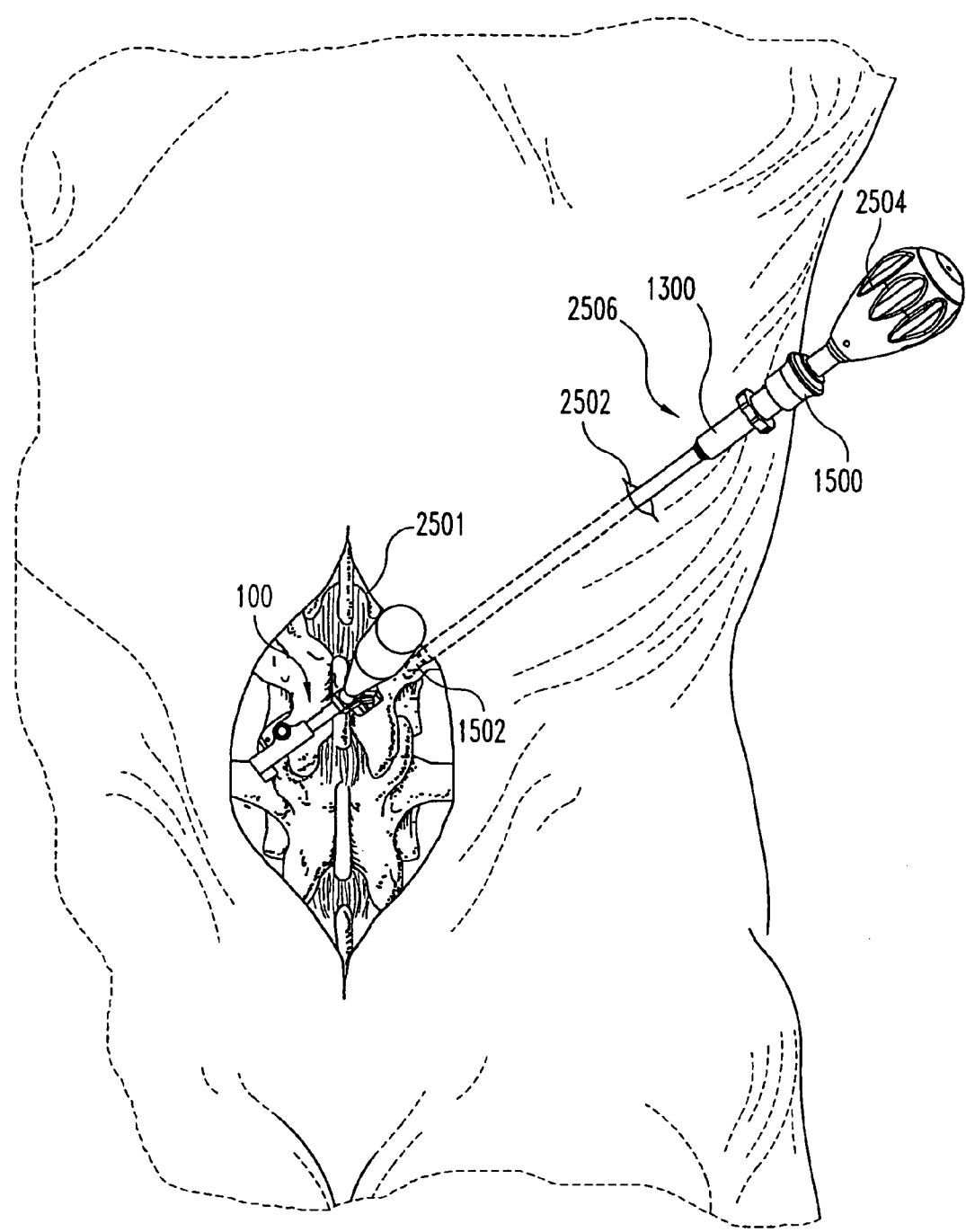
FIG. 25 is a top view of a treatment site incision opening in a prone patient shown fragmentarily, and showing the screw placement guide clamped to the adjacent vertebrae along with a guide tube and trocar inserted through a second percutaneous incision in the patient.
Figure 26:
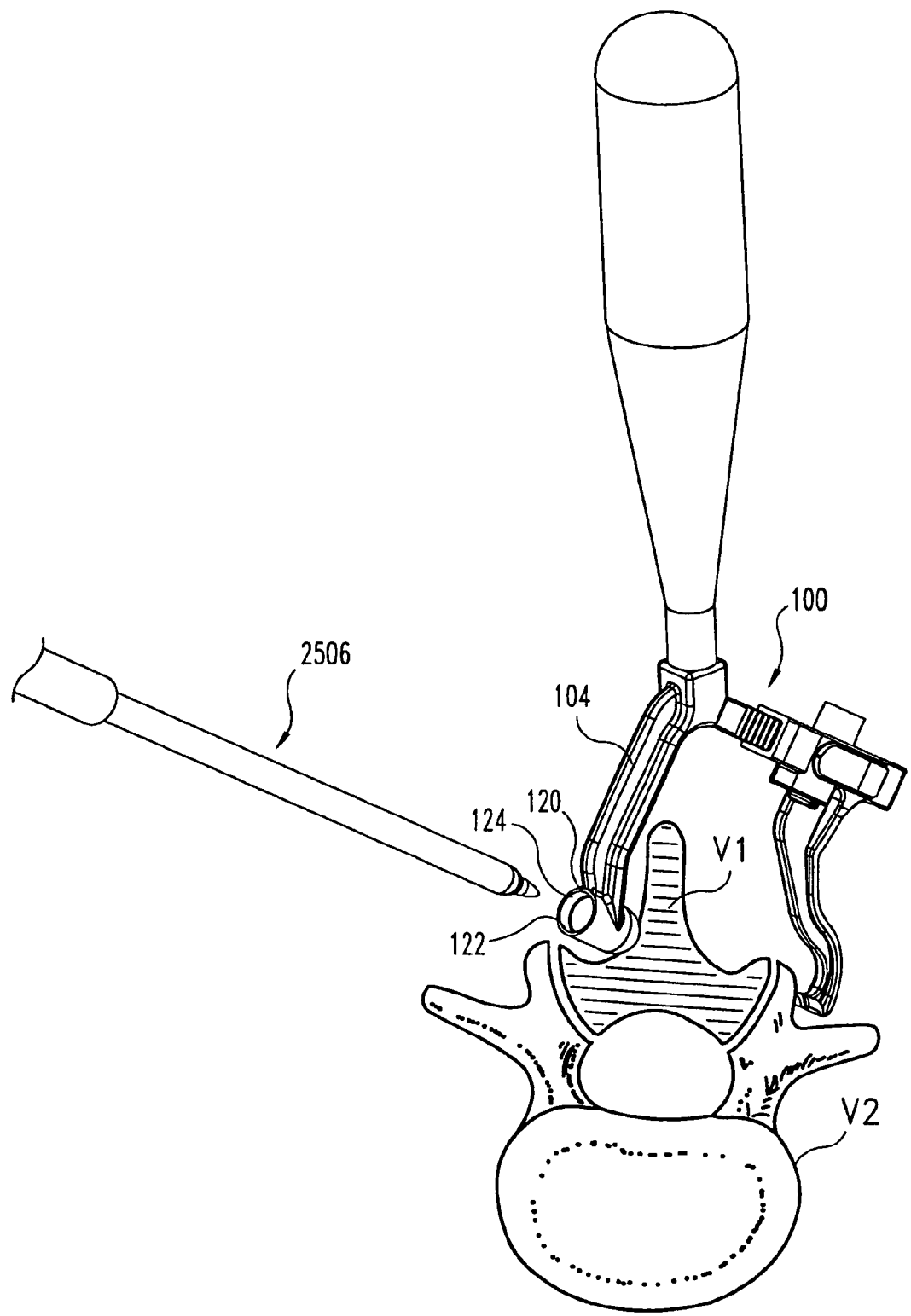
FIG. 26 is a partial cross-sectional view of a vertebra showing the screw placement guide along with the guide tube and trocar.

Referring specifically to FIG. 25, at the beginning of the procedure, a first incision 2501 is initially made over the affected portion of the spine. As described above, screw placement guide 100 is then positioned and clamped to the adjacent vertebrae V1 and V2. The clamped orientation of guide 100 indicates to the surgeon where a second percutaneous incision 2502 should be made. After the second percutaneous incision 2502 is made, as shown in FIG. 25, guide tube 1300 along with trocar 1500 are inserted into second incision 2502. A handle 2504 is removably coupled to coupling portion 1504 of trocar 1500 for guiding trocar and guide assembly 2506. Pointed end 1502 of trocar 1500 helps guide 1300 to move from second incision 2502 to first incision 2501. The trocar guide assembly 2506 is then inserted into hole 122 of guide 120. Conical walls 124 aid insertion of guide 1300 into guide 120 (FIG. 26).

Figure 27:
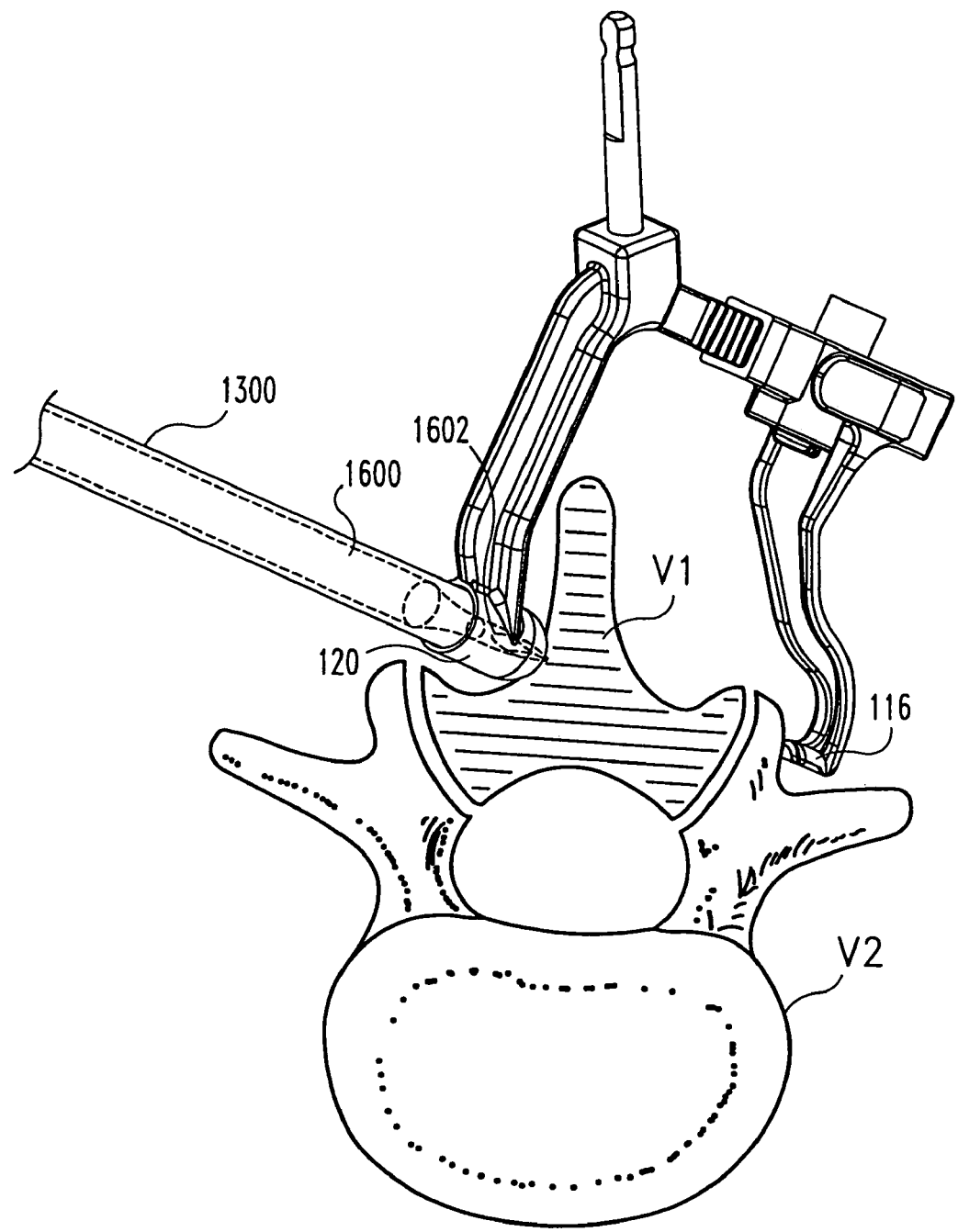
FIG. 27 is a partial cross-sectional view of a vertebra, showing an awl ready for marking a starting point on the vertebra.
Figure 28:
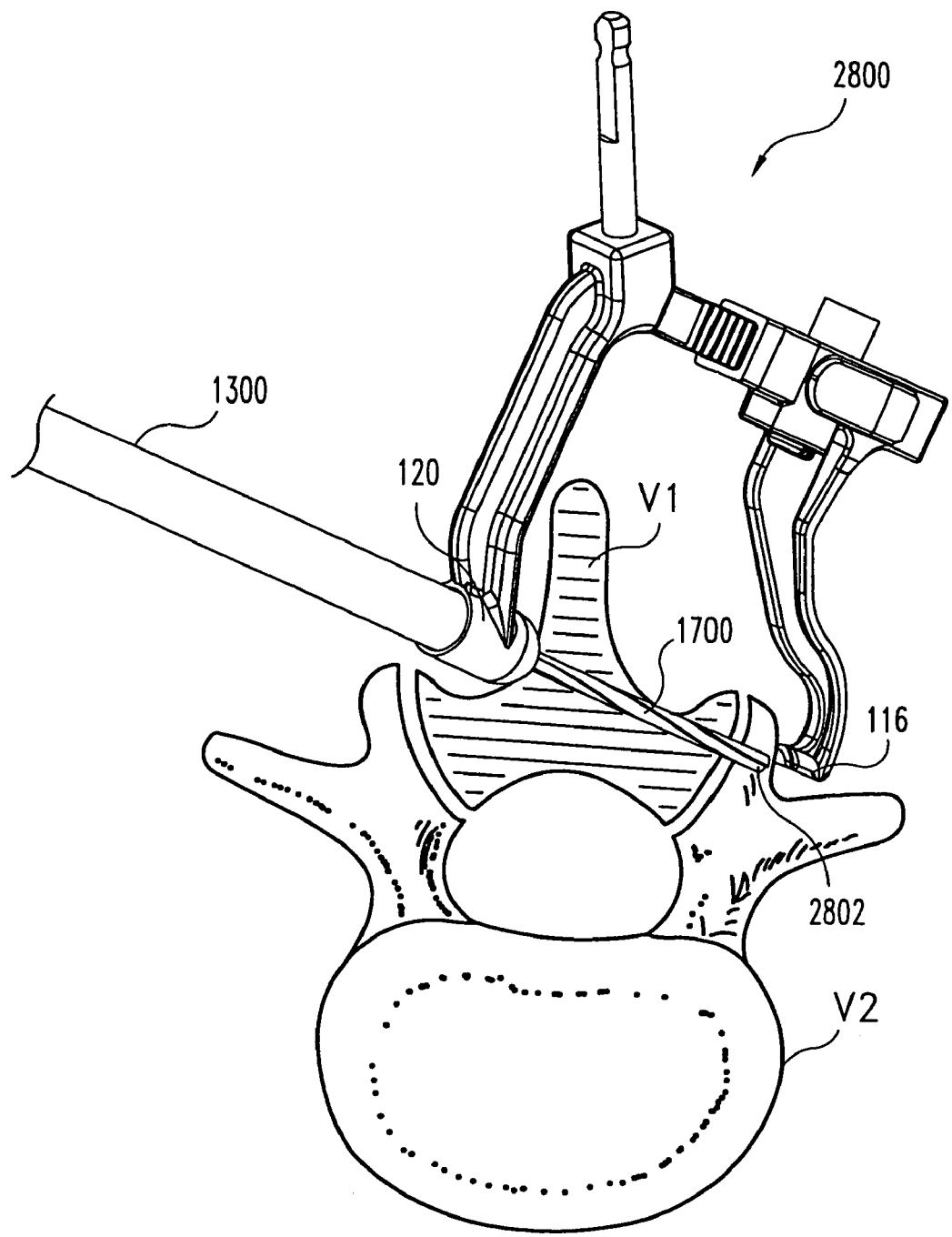
FIG. 28 is a partial cross-sectional view of a drill bit inside the vertebra.
Figure 29:
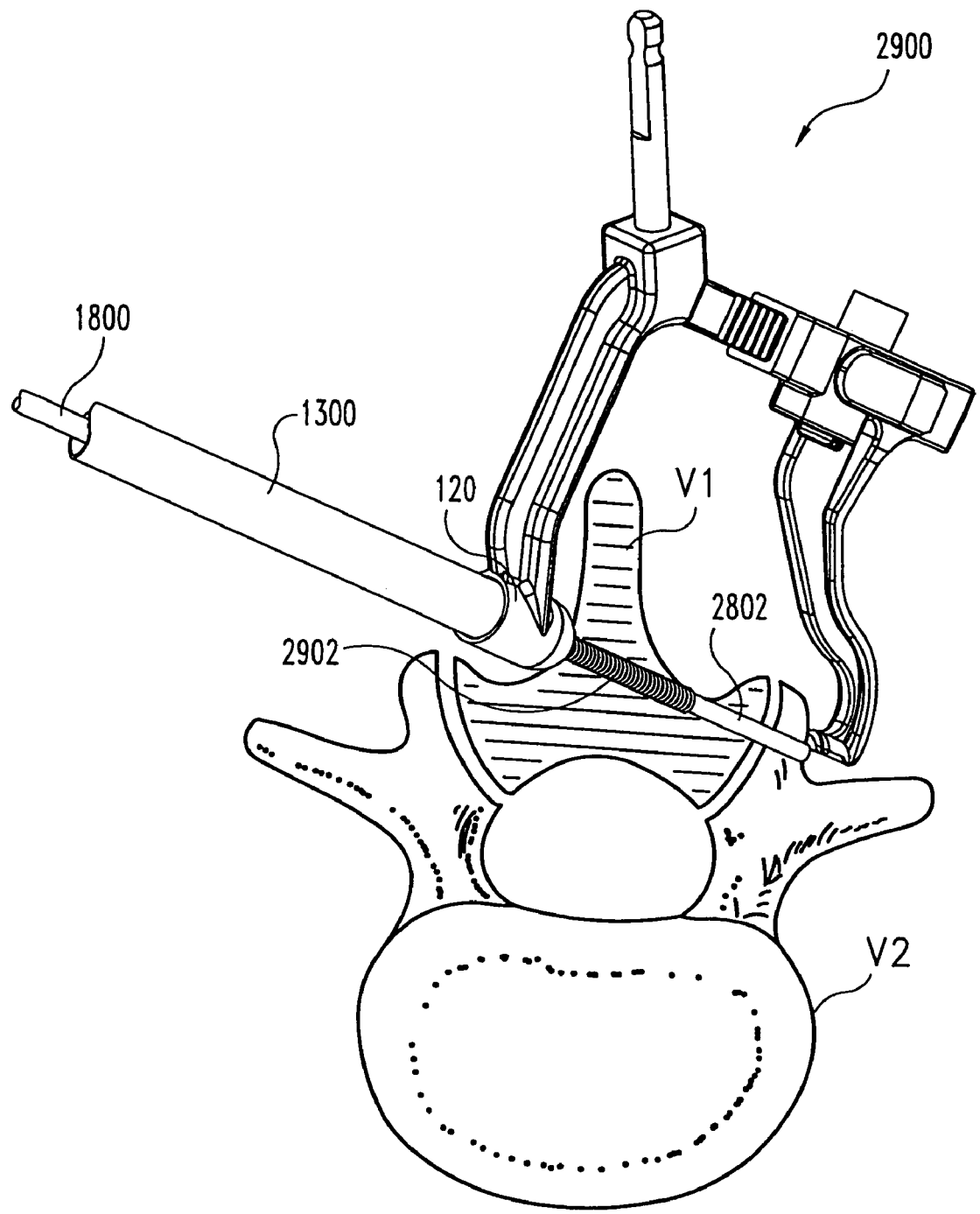
FIG. 29 is a partial cross-sectional view of a screw threaded into the vertebra.

After the guide tube 1300 is snuggly fitted into guide 120, trocar 1500 is removed from guide tube 1300. Awl 1600 is then inserted into guide tube and the pointed portion 1602 is pressed against vertebra V1 in order to make a starting mark as shown in FIG. 27. The starting mark etched by awl 1600 helps to minimize drill bit cutting portion 1702 slippage when drilling is started. In stage 2800, as shown in FIG. 28, awl 1600 is removed, and drill bit 1700 is then inserted into guide tube 1300. Drill bit 1700 creates a hole 2802 through which the screw 2902 is set in stage 2900 after hole 2802 is drilled. Screwdriver 1800 drives screw 2902 into V1 and V2 to fasten the adjacent vertebrae V1 and V2 together (FIG. 29).

Figure 30:
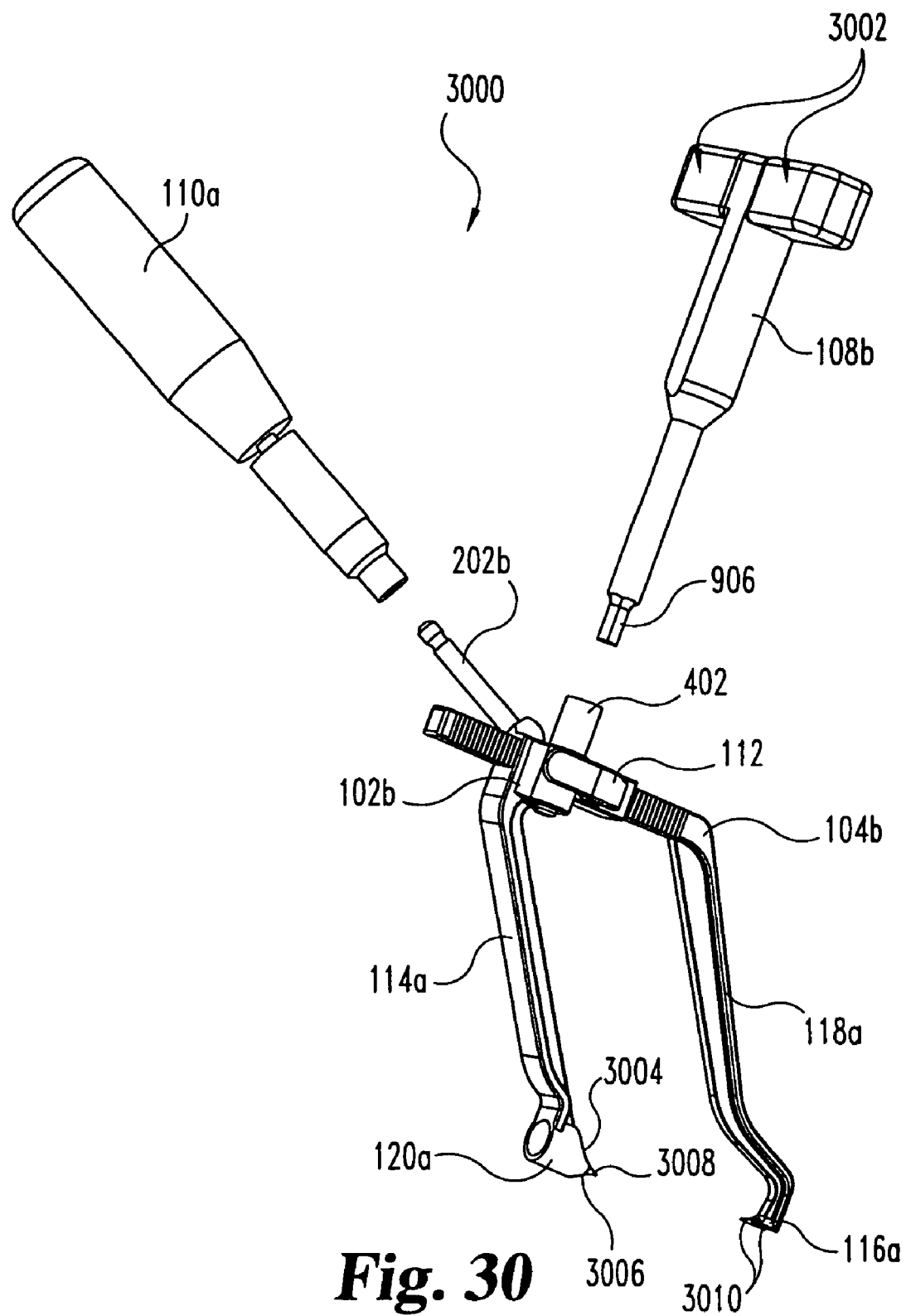
FIG. 30 is an exploded-perspective view of a screw placement guide according to another embodiment of the present invention.
Figure 31:
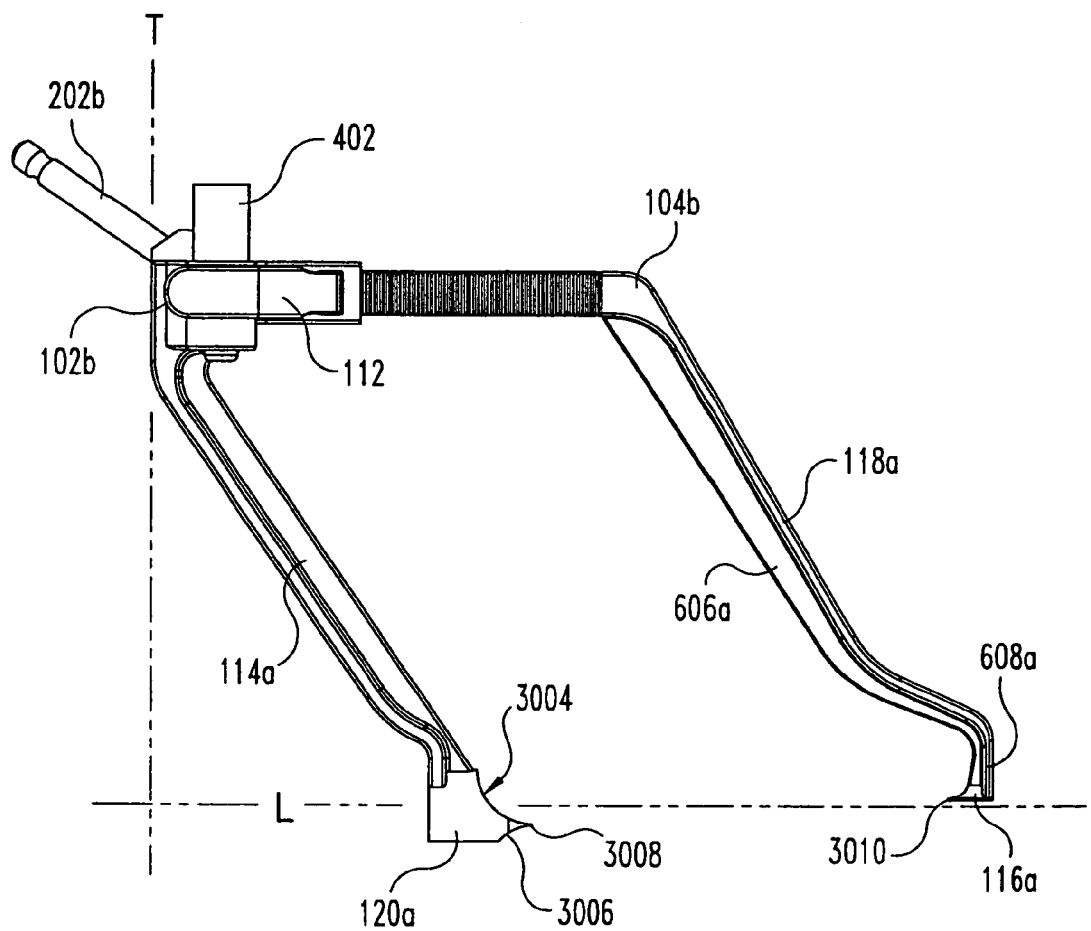
FIG. 31 is a side view of the screw placement guide shown in FIG. 30 without a handle and a driver.
Figure 32:
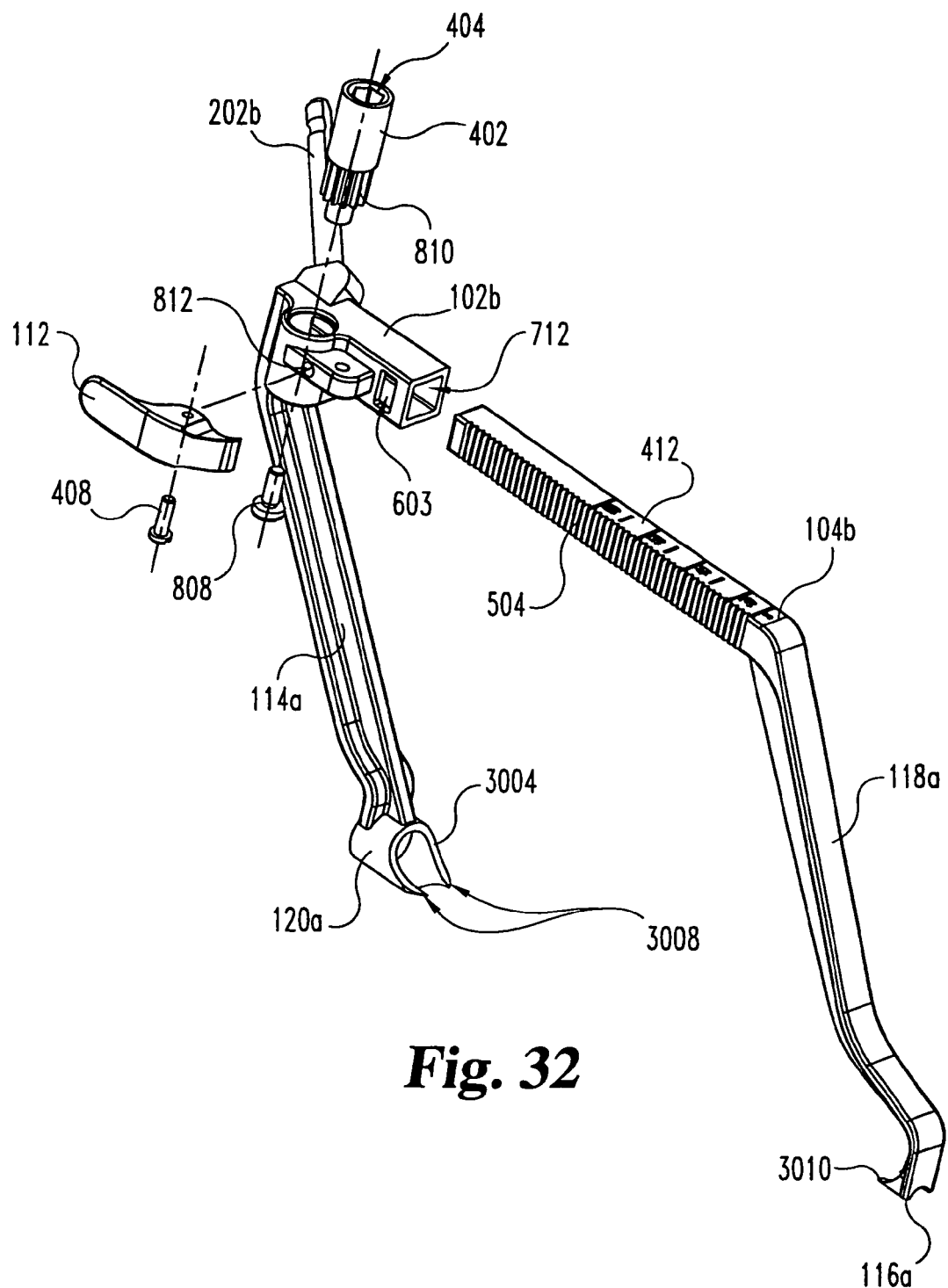
FIG. 32 is an exploded perspective view of the screw placement guide shown in FIG. 31.

A screw placement guide 3000 according to another embodiment of the present invention is illustrated in FIGS. 30–32. A driver 108b with a pinion-engaging portion 906 is removably coupled to pinion 402. Driver 108b includes a pair of handle members 3002 that extend therefrom. Handle 110a is removably coupled to handle coupling member 202b. Handle coupling member 202b is attached to a first member 102b, and the first member 102b is moveably coupled to a second member 104b. As illustrated in FIGS.

31–32, handle coupling member 202b is oriented at an angle with respect to both transverse axis T and a plane containing axes T and L in order to improve the ergonomics of the handle 202b. As can be appreciated from the illustrations, the angulation increases the distance between 110a and driver 108b thereby increasing the ease of use.

Further, the angulation of handle coupling member 202b positions handle 110a out of the surgical field and improves surgeon visibility. Since surgical access to the spine may be relatively small in size, it is preferable to have substantially unobstructed access to view the surgical site. This may be particularly relevant when it is necessary to view guide tube placement or depth markings on cutting instruments.

First member 102b has a locking mechanism 112 and a first support arm 114a that supports a cylindrical guide member 120a. Second member 104b has a second support arm 118a that supports an arcuate guide member 116a. Second support arm 118a has an angled portion 606a and a guide connecting portion 608a. As shown in FIG. 31, first support arm 114a and the angled portion 606a of the second support arm 118a are oriented parallel with respect to one another and at an angle with respect to transverse axis T. In a preferred embodiment this angle may be between 15 degrees and 55 degrees. In the illustrated embodiment, the angle is substantially 35 degrees. Further, first support arm 114a and angled portion 606a have been lengthened to provide at least two advantages. First, the angulation and lengthening allows the locking mechanism 112 and handle coupling member 202b to extend out of the surgical site. This provides easier access to these components for the surgeon. Second, the greater length of the arms provides more clearance for the spinous process. Second member 104b further has length markings 412 defined thereon and a rack portion 504 that engages teeth 810 on pinion 402.

The cylindrical guide member 120a has an upper curved bone-engaging portion 3004 and a lower curved bone-engaging portion 3006. Both curved portions 3004 and 3006 intersect to form a pair of pointed bone engagement portions 3008. Likewise, arcuate guide member 116a has a pair of pointed bone engagement portions 3010. This configuration improves the contact between the guide 3000 and vertebral bone.

Figure 33:
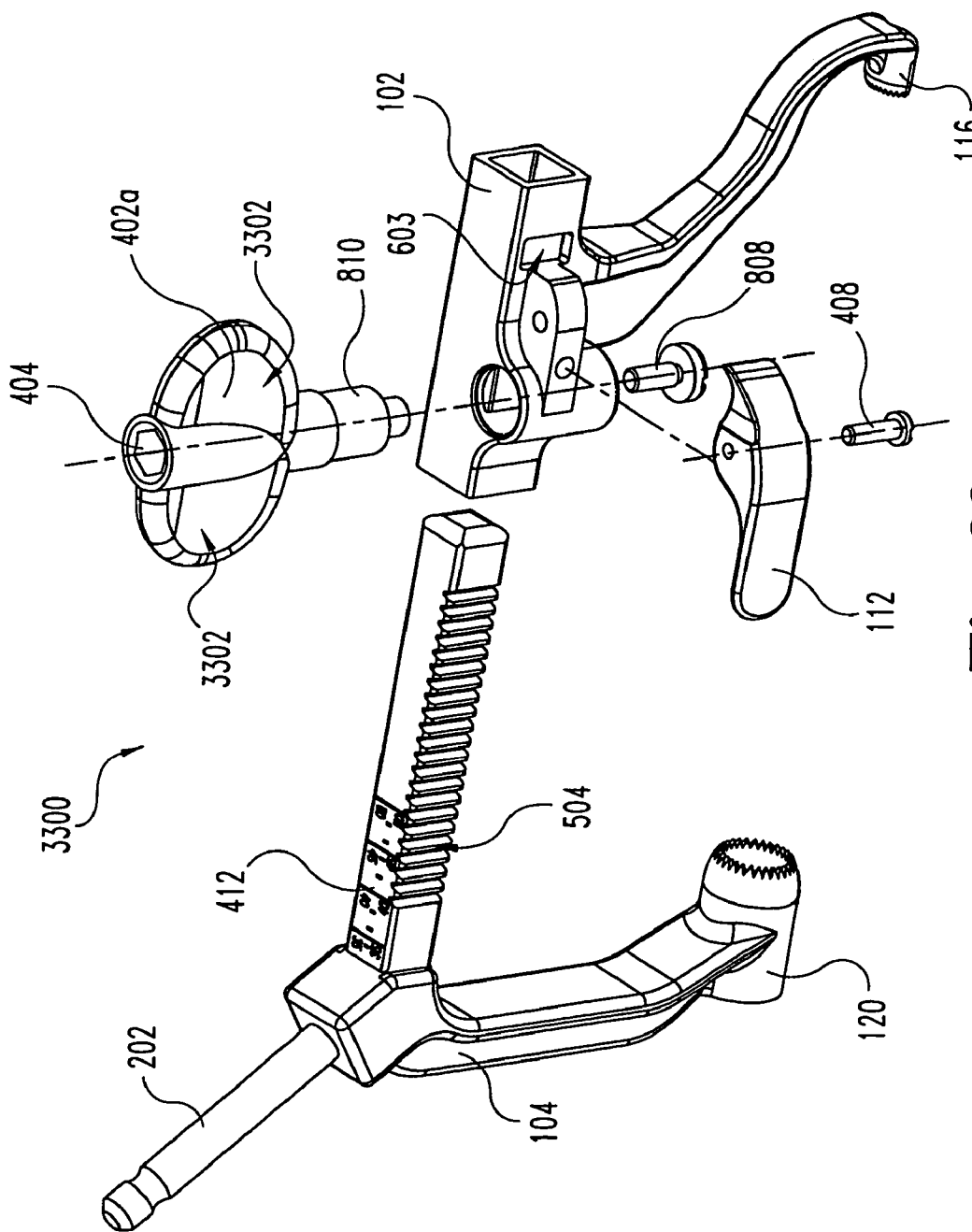
FIG. 33 is an exploded perspective view of a screw placement guide according to a further embodiment of the present invention.

A screw placement guide 3300 according to still yet another embodiment is illustrated in FIG. 33. In this particular embodiment, the guide 3300 has a pinion 402a with a pair of lever members 3302 extending therefrom. The pinion 402a further has a driver engagement recess 404 defined therein. The pinion 402a can be rotated with the lever members 3302 and/or with a driver 108 engaged to the driver engagement recess 404.

Figure 34:
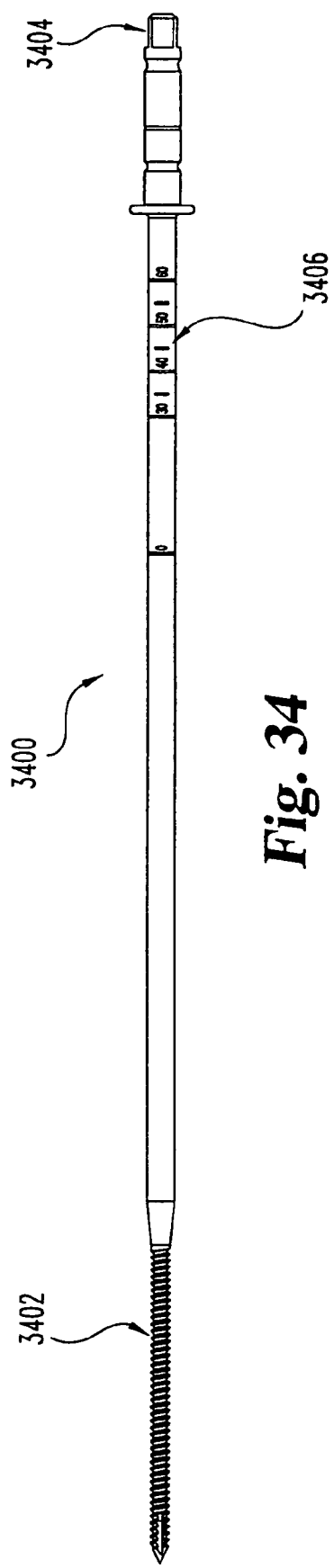
FIG. 34 is a side view of a tap.
Figure 35:
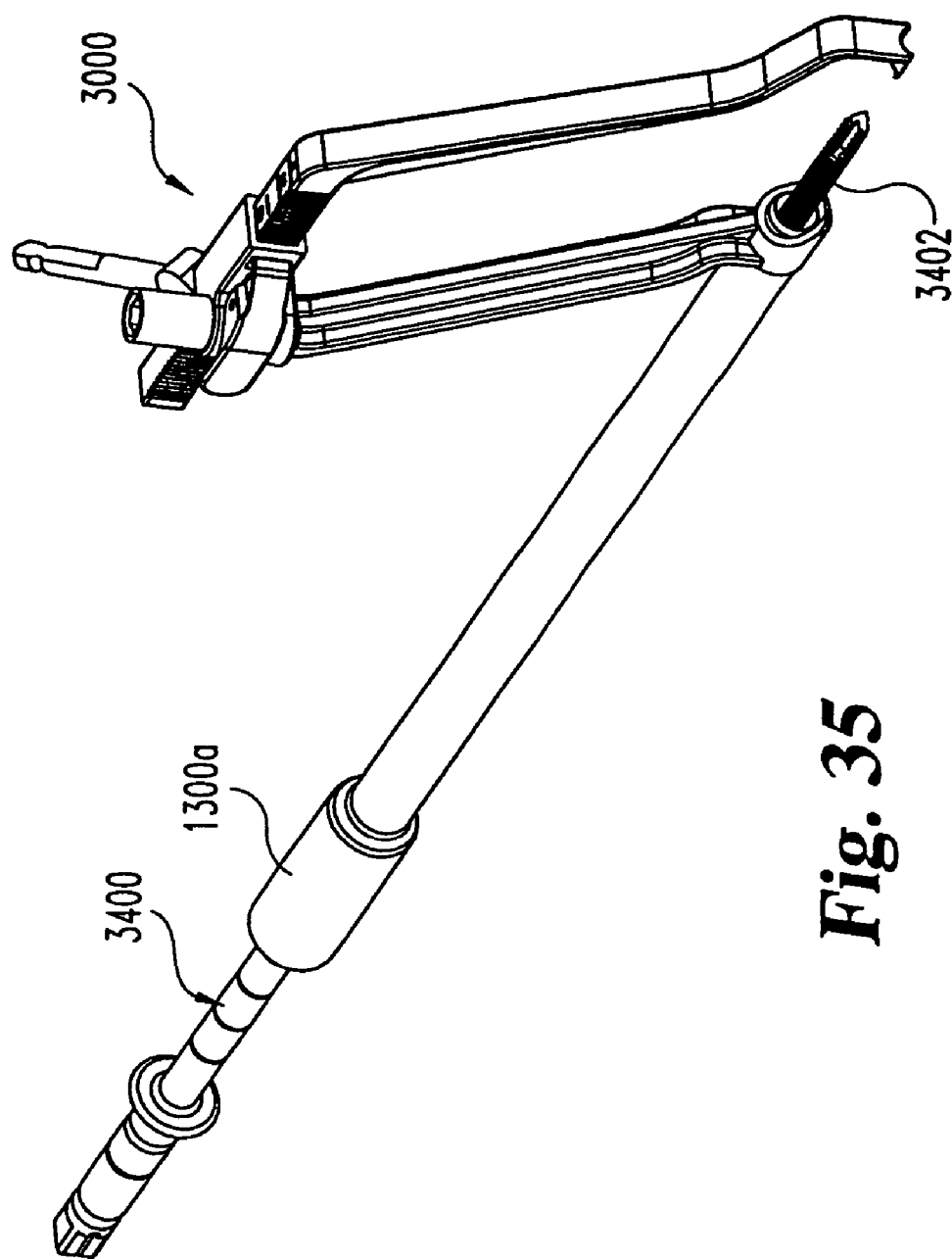
FIG. 35 is a perspective view of the tap of FIG. 34 inserted in a guide tube that is coupled to the screw placement guide of FIG. 30.

A tap 3400 that can be used in conjunction with the above-described screw placement guides is depicted in FIGS. 34–35. Tap 3400 includes a thread cutting portion 3402 and a coupling end 3404 that is adapted to coupled to a handle and/or other types of generally known driving mechanisms. Tap 3400 further includes depth markings 3406 that indicate the depth of the tap 3400. As shown in FIG. 35, tap 3400 is inserted into a guide tube 1300a that is coupled to the screw placement guide 3000. The tap 3400 is used to form threads in the hole 2802 after the hole 2802 is drilled into the vertebrae V1 and V2 (FIG. 28). Afterwards, the screw 2902 is threaded onto the threads formed in the hole 2802.

While specific embodiments of the present invention have been shown and described in detail, the breadth and scope of the present invention should not be limited by the above described exemplary embodiments, but should be defined only in accordance with the following claims and their equivalents. All changes and modifications that come within the spirit of the invention are desired to be protected.

What is claimed is:

1. An apparatus for guiding a fastener that fastens a first vertebral bone portion with a second vertebral bone portion, comprising:
    a first member having a first guide adapted to contact the first vertebral bone portion, wherein said first guide has a semi-cylindrical shape;
    a second member having a second guide aligned with said first guide and adapted to contact the second vertebral bone portion; and
    a clamping mechanism provided between said first and second members to clamp said first guide to said first bone portion and said second guide to said second bone portion, wherein said first guide and said second guide are aligned to indicate fastener alignment.

2. The apparatus of claim 1, wherein one of said first and second members includes a handle receiving member and a handle removably coupled to said handle receiving member.

3. The apparatus of claim 1, further comprising a locking mechanism to lock relative position between said first and second members.

4. The apparatus of claim 1, wherein said first guide is adapted to receive a guide tube.

5. The apparatus of claim 1, further comprising a handle provided on one of said first and second members.

6. The apparatus of claim 1, further comprising a handle provided on said first member and a locking mechanism provided on said first member.

7. The apparatus of claim 1, further comprising a guide tube coupled to said second guide.

8. The apparatus of claim 7, farther comprising a trocar provided in said guide tube.

9. The apparatus of claim 7, further comprising an awl provided in said guide tube for cutting bone.

10. The apparatus of claim 7, further comprising a drill bit provided in said guide tube.

11. The apparatus of claim 10, wherein said drill bit includes depth indicators provided thereon.

12. The apparatus of claim 7, further comprising a screw driver provided in said guide tube.

13. The apparatus of claim 12, wherein said screw driver has a self-retaining screw head.

14. The apparatus of claim 12, wherein said screw driver has a hexagonal head.

15. The apparatus of claim 1, further comprising a tap provided in said guide tube.

16. The apparatus of claim 1, wherein said clamping mechanism clamps the first vertebral bone portion and the second vertebral bone portion together.

17. The apparatus of claim 1, wherein said clamping mechanism accommodates varying anatomy.

18. The apparatus of claim 1, wherein said first guide is arcuate.

19. The apparatus of claim 1, wherein said second guide defines an axis along which the fastener is positioned and said first guide is offset from said axis.

20. An apparatus for guiding a fastener that fastens a first vertebral bone portion with a second vertebral bone portion, comprising:
    a first member having a first guide adapted to contact the first vertebral bone portion,
    a second member having a second guide aligned with said first guide and adapted to contact the second vertebral bone portion; and a clamping mechanism provided between said first and second members to clamp said first guide to said first bone portion and said second guide to said second bone portion, wherein said first guide and said second guide are aligned to indicate fastener alignment, wherein first member includes an elongated support arm supporting said first guide at one end thereof and said second member includes an elongated support arm supporting said second guide at one end thereof, said first and second support arms extending parallel to another.

21. An apparatus for guiding a fastener that fastens a first vertebral bone portion with a second vertebral bone portion, comprising:
   a first member having first guide adapted to contact the first vertebral bone portion;
   a second member having a second guide aligned with the first guide and adapted to contact the second vertebral bone portion;
   a clamping mechanism provided between said first and second members to clamp said first guide to said first bone portion and said second guide to said second bone portion, wherein:
      said first guide and said second guide are aligned to indicate fastener alignment; and
      said second guide defines an axis along which the fastener is positioned and said first guide is offset from said axis.

22. The apparatus of claim 21, wherein one of said first and second members includes a handle receiving member and a handle removably coupled to said handle receiving member.

23. The apparatus of claim 21, further comprising a locking mechanism to lock relative position between said first and second members.

24. The apparatus of claim 21, wherein said first guide is adapted to receive a guide tube.

25. The apparatus of claim 21, further comprising a handle provided on one of said first and second members.

26. The apparatus of claim 21, further comprising a handle provided on said first member and a locking mechanism provided on said first member.

27. The apparatus of claim 21, wherein said first guide has a semi-cylindrical shape.

\* \* \* \* \*